United States Patent
Collard et al.

(10) Patent No.: US 8,936,648 B2
(45) Date of Patent: Jan. 20, 2015

(54) KNEE JOINT PROSTHESIS SYSTEM AND METHOD FOR IMPLANTATION

(71) Applicant: Biomet Manufacturing Corporation, Warsaw, IN (US)

(72) Inventors: Curt Collard, Warsaw, IN (US); Michael John Collins, Swindon (GB); Robert Metzger, Wakarusa, IN (US); Brian M. May, Warsaw, IN (US); Larabeth G. Ryan, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/796,440

(22) Filed: Mar. 12, 2013

(65) Prior Publication Data

US 2013/0190883 A1 Jul. 25, 2013

Related U.S. Application Data

(63) Continuation-in-part of application No. 13/564,848, filed on Aug. 2, 2012, now Pat. No. 8,480,751, which is a continuation of application No. 12/729,852, filed on Mar. 23, 2010, now Pat. No. 8,328,873, which is a (Continued)

(51) Int. Cl.
*A61F 2/38* (2006.01)
*A61F 2/30* (2006.01)

(52) U.S. Cl.
CPC ..... *A61F 2/3836* (2013.01); *A61F 2002/30344* (2013.01); *A61F 2002/30364* (2013.01); *A61F 2/385* (2013.01); *A61F 2/3868* (2013.01); *A61F 2002/3069* (2013.01); *A61F 2002/30616* (2013.01); *A61F 2002/30736* (2013.01);
(Continued)

(58) Field of Classification Search
USPC ............................................ 623/20.14–20.36
See application file for complete search history.

(56) References Cited

U.S. PATENT DOCUMENTS

| 538,987 A | 5/1895 | Turley |
| 3,806,961 A | 4/1974 | Muller et al. |

(Continued)

FOREIGN PATENT DOCUMENTS

| DE | 3336004 A1 | 6/1985 |
| EP | 0000549 A1 | 2/1979 |

(Continued)

OTHER PUBLICATIONS

"Advantim® Total Knee System," brochure,1996 (pp. 1-14) Wright Medical Technology, Inc.

(Continued)

*Primary Examiner* — Yashita Sharma
(74) *Attorney, Agent, or Firm* — Harness, Dickey

(57) ABSTRACT

A prosthesis for replacing a knee joint between a femur and a tibia can include a femoral component, a tibial component, a bearing and a yoke assembly. The yoke assembly can have a yoke disposed between the bearing and the femoral component and an axle having an axle axis. The axle can hingedly couple the yoke with the femoral component. Rotation of the femoral component about a rotation axis that is perpendicular to the axle axis causes concurrent rotation of the yoke about the rotation axis.

13 Claims, 11 Drawing Sheets

Related U.S. Application Data continuation-in-part of application No. 12/536,056, filed on Aug. 5, 2009, now Pat. No. 8,163,028, which is a continuation-in-part of application No. 11/972,359, filed on Jan. 10, 2008, now Pat. No. 8,157,869.

(60) Provisional application No. 60/978,949, filed on Oct. 10, 2007, provisional application No. 60/879,733, filed on Jan. 10, 2007.

(52) U.S. Cl.
CPC .......... *A61F2220/0025* (2013.01); *A61F 2002/30604* (2013.01); *A61F 2/38* (2013.01); *A61F 2002/30332* (2013.01); *A61F 2002/30369* (2013.01); *A61F 2220/0033* (2013.01); *A61F 2/30721* (2013.01); *A61F 2002/30507* (2013.01); *A61F 2002/30878* (2013.01)
USPC .............. 623/20.29; 623/20.14; 623/20.21; 623/20.24; 623/20.27; 623/20.28; 623/20.31; 623/20.32; 623/20.33

(56) References Cited

U.S. PATENT DOCUMENTS

| | | | |
|---|---|---|---|
| 3,848,272 | A | 11/1974 | Noiles |
| 3,859,992 | A | 1/1975 | Amstutz |
| 3,878,566 | A | 4/1975 | Bechtol |
| 3,964,106 | A | 6/1976 | Hutter, Jr. et al. |
| 4,001,897 | A | 1/1977 | Rambert et al. |
| 4,007,495 | A | 2/1977 | Frazier |
| 4,012,796 | A | 3/1977 | Weisman et al. |
| 4,041,550 | A | 8/1977 | Frazier |
| 4,064,567 | A | 12/1977 | Burstein et al. |
| 4,136,405 | A | 1/1979 | Pastrick et al. |
| 4,151,615 | A | 5/1979 | Hall |
| 4,202,055 | A | 5/1980 | Reiner et al. |
| 4,219,893 | A | 9/1980 | Noiles |
| 4,224,698 | A | 9/1980 | Hopson |
| 4,284,080 | A | 8/1981 | Rehder et al. |
| 4,305,394 | A | 12/1981 | Bertuch, Jr. |
| 4,344,192 | A | 8/1982 | Imbert et al. |
| 4,404,691 | A | 9/1983 | Buning et al. |
| 4,475,549 | A | 10/1984 | Oh |
| RE31,865 | E | 4/1985 | Roux |
| 4,523,587 | A | 6/1985 | Frey |
| 4,549,319 | A | 10/1985 | Meyer |
| 4,579,558 | A | 4/1986 | Ramer |
| 4,619,658 | A | 10/1986 | Pappas et al. |
| 4,624,674 | A | 11/1986 | Pappas et al. |
| 4,632,111 | A | 12/1986 | Roche |
| 4,655,777 | A | 4/1987 | Dunn et al. |
| 4,659,331 | A | 4/1987 | Matthews et al. |
| 4,661,112 | A | 4/1987 | Muller |
| 4,676,797 | A | 6/1987 | Anapliotis et al. |
| 4,676,798 | A | 6/1987 | Noiles |
| 4,676,799 | A | 6/1987 | Legrand |
| 4,678,470 | A | 7/1987 | Nashef et al. |
| 4,698,063 | A | 10/1987 | Link et al. |
| 4,711,233 | A | 12/1987 | Brown |
| 4,711,639 | A | 12/1987 | Grundei |
| 4,714,477 | A | 12/1987 | Fichera et al. |
| 4,716,894 | A | 1/1988 | Lazzeri et al. |
| 4,718,909 | A | 1/1988 | Brown |
| 4,718,911 | A | 1/1988 | Kenna |
| 4,718,915 | A | 1/1988 | Epinette |
| 4,718,916 | A | 1/1988 | Morscher |
| 4,728,333 | A | 3/1988 | Masse et al. |
| 4,735,625 | A | 4/1988 | Davidson |
| 4,737,411 | A | 4/1988 | Graves, Jr. et al. |
| 4,764,171 | A | 8/1988 | Harder et al. |
| 4,770,658 | A | 9/1988 | Geremakis |
| 4,770,659 | A | 9/1988 | Kendall |
| 4,770,660 | A | 9/1988 | Averill |
| 4,770,661 | A | 9/1988 | Oh |
| 4,778,473 | A | 10/1988 | Matthews et al. |
| 4,778,474 | A | 10/1988 | Homsy |
| 4,784,662 | A | 11/1988 | Muller |
| 4,784,663 | A | 11/1988 | Kenna |
| 4,789,663 | A | 12/1988 | Wallace et al. |
| 4,790,852 | A | 12/1988 | Noiles |
| 4,790,854 | A | 12/1988 | Harder et al. |
| 4,795,470 | A | 1/1989 | Goymann et al. |
| 4,795,471 | A | 1/1989 | Oh |
| 4,798,610 | A | 1/1989 | Averill et al. |
| 4,801,301 | A | 1/1989 | Noiles |
| 4,813,961 | A | 3/1989 | Sostegni |
| 4,822,366 | A | 4/1989 | Bolesky |
| 4,827,919 | A | 5/1989 | Barbarito et al. |
| 4,828,566 | A | 5/1989 | Griss |
| 4,842,606 | A | 6/1989 | Kranz et al. |
| 4,846,839 | A | 7/1989 | Noiles |
| 4,846,840 | A | 7/1989 | Leclercq et al. |
| 4,851,007 | A | 7/1989 | Gray |
| 4,871,368 | A | 10/1989 | Wagner |
| 4,878,916 | A | 11/1989 | Rhenter et al. |
| 4,883,488 | A | 11/1989 | Bloebaum et al. |
| 4,883,492 | A | 11/1989 | Frey et al. |
| 4,888,021 | A | 12/1989 | Forte et al. |
| 4,892,547 | A | 1/1990 | Brown |
| 4,904,265 | A | 2/1990 | MacCollum et al. |
| 4,908,033 | A | 3/1990 | Frey et al. |
| 4,908,034 | A | 3/1990 | Weightman et al. |
| 4,908,036 | A | 3/1990 | Link et al. |
| 4,911,723 | A | 3/1990 | Menschik |
| 4,919,674 | A | 4/1990 | Schelhas |
| 4,923,472 | A | 5/1990 | Ugolini |
| 4,936,847 | A | 6/1990 | Manginelli |
| 4,936,853 | A | 6/1990 | Fabian et al. |
| 4,936,855 | A | 6/1990 | Sherman |
| 4,936,861 | A | 6/1990 | Muller et al. |
| 4,938,769 | A | 7/1990 | Shaw |
| 4,938,772 | A | 7/1990 | Frey et al. |
| 4,944,756 | A | 7/1990 | Kenna |
| 4,944,757 | A | 7/1990 | Martinez et al. |
| 4,950,297 | A | 8/1990 | Elloy et al. |
| 4,950,298 | A | 8/1990 | Gustilo et al. |
| 4,950,299 | A | 8/1990 | Noiles |
| 4,959,071 | A | 9/1990 | Brown et al. |
| 4,960,427 | A | 10/1990 | Noiles |
| 4,961,748 | A | 10/1990 | Frey et al. |
| 4,963,154 | A | 10/1990 | Anapliotis et al. |
| 4,963,155 | A | 10/1990 | Lazzeri et al. |
| 4,964,869 | A | 10/1990 | Auclair et al. |
| 4,978,356 | A | 12/1990 | Noiles |
| 4,985,037 | A | 1/1991 | Petersen |
| 4,990,161 | A | 2/1991 | Kampner |
| 4,994,064 | A | 2/1991 | Aboczky |
| 4,995,158 | A | 2/1991 | Howell et al. |
| 4,995,883 | A | 2/1991 | Demane et al. |
| 5,002,578 | A | 3/1991 | Luman |
| 5,002,581 | A | 3/1991 | Paxson et al. |
| 5,009,666 | A | 4/1991 | Van Syckle et al. |
| 5,019,103 | A | 5/1991 | Van Zile et al. |
| 5,019,105 | A | 5/1991 | Wiley |
| 5,019,108 | A | 5/1991 | Bertin et al. |
| 5,021,062 | A | 6/1991 | Adrey et al. |
| 5,030,221 | A | 7/1991 | Buechel et al. |
| 5,032,134 | A | 7/1991 | Lindwer |
| 5,037,424 | A | 8/1991 | Aboczsky |
| 5,037,438 | A | 8/1991 | Davidson |
| 5,037,441 | A | 8/1991 | Bouvet |
| 5,041,140 | A | 8/1991 | Teinturier |
| 5,061,269 | A | 10/1991 | Muller |
| 5,061,270 | A | 10/1991 | Aboczky |
| 5,062,852 | A | 11/1991 | Dorr et al. |
| 5,062,853 | A | 11/1991 | Forte |
| 5,074,879 | A | 12/1991 | Pappas et al. |
| 5,080,677 | A | 1/1992 | Shelley |
| 5,084,051 | A | 1/1992 | Tormala et al. |
| 5,092,900 | A | 3/1992 | Marchetti et al. |
| 5,098,437 | A | 3/1992 | Kashuba et al. |
| 5,108,437 | A | 4/1992 | Kenna |
| 5,108,439 | A | 4/1992 | Morscher et al. |
| 5,108,445 | A | 4/1992 | Ashby |

(56) References Cited

U.S. PATENT DOCUMENTS

| | | |
|---|---|---|
| 5,108,446 A | 4/1992 | Wagner et al. |
| 5,108,450 A | 4/1992 | Horber et al. |
| 5,112,338 A | 5/1992 | Anspach, III |
| 5,116,339 A | 5/1992 | Glock |
| 5,116,378 A | 5/1992 | Carbone |
| 5,116,379 A | 5/1992 | McLardy-Smith |
| 5,116,380 A | 5/1992 | Hewka et al. |
| 5,133,760 A | 7/1992 | Petersen et al. |
| 5,133,763 A | 7/1992 | Mullers |
| 5,137,535 A | 8/1992 | Keller |
| 5,137,536 A | 8/1992 | Koshino |
| 5,141,512 A | 8/1992 | Farmer et al. |
| 5,147,406 A | 9/1992 | Houston et al. |
| 5,152,796 A | 10/1992 | Slamin |
| 5,152,797 A | 10/1992 | Luckman et al. |
| 5,163,963 A | 11/1992 | Hewka et al. |
| 5,163,966 A | 11/1992 | Norton et al. |
| 5,169,399 A | 12/1992 | Ryland et al. |
| 5,171,243 A | 12/1992 | Kashuba et al. |
| 5,171,276 A | 12/1992 | Caspari et al. |
| 5,171,286 A | 12/1992 | Lawes et al. |
| 5,171,313 A | 12/1992 | Salyer |
| 5,171,323 A | 12/1992 | Willert et al. |
| 5,176,709 A | 1/1993 | Branemark |
| 5,180,394 A | 1/1993 | Davidson |
| 5,181,925 A | 1/1993 | Houston et al. |
| 5,181,929 A | 1/1993 | Prats et al. |
| 5,192,331 A | 3/1993 | Spotorno et al. |
| 5,194,066 A | 3/1993 | Van Zile |
| 5,197,488 A | 3/1993 | Kovacevic |
| 5,197,987 A | 3/1993 | Koch et al. |
| 5,197,988 A | 3/1993 | Spotorno et al. |
| 5,201,769 A | 4/1993 | Schutzer |
| 5,211,664 A | 5/1993 | Tepic et al. |
| 5,211,666 A | 5/1993 | Fetto |
| 5,217,496 A | 6/1993 | Bruce et al. |
| 5,217,498 A | 6/1993 | Henssge et al. |
| 5,219,362 A | 6/1993 | Tuke et al. |
| 5,222,983 A | 6/1993 | Schmitz et al. |
| 5,222,984 A | 6/1993 | Forte |
| 5,226,915 A | 7/1993 | Bertin |
| 5,242,445 A | 9/1993 | Ashman |
| 5,246,459 A | 9/1993 | Elias |
| 5,250,051 A | 10/1993 | Maryan |
| 5,258,034 A | 11/1993 | Furlong et al. |
| 5,258,035 A | 11/1993 | Hofmann et al. |
| 5,263,988 A | 11/1993 | Huebner |
| 5,275,601 A | 1/1994 | Gogolewski et al. |
| 5,282,867 A | 2/1994 | Mikhail |
| 5,282,870 A | 2/1994 | Moser et al. |
| 5,284,483 A | 2/1994 | Johnson et al. |
| 5,290,311 A | 3/1994 | Baumann |
| 5,290,313 A | 3/1994 | Heldreth |
| 5,290,315 A | 3/1994 | DeCarlo, Jr. |
| 5,290,318 A | 3/1994 | Ling et al. |
| 5,292,322 A | 3/1994 | Faccioli et al. |
| 5,314,478 A | 5/1994 | Oka et al. |
| 5,314,479 A | 5/1994 | Rockwood, Jr. et al. |
| 5,314,491 A | 5/1994 | Thongpreda et al. |
| 5,318,571 A | 6/1994 | Benson |
| 5,320,625 A | 6/1994 | Bertin |
| 5,326,358 A | 7/1994 | Aubriot et al. |
| 5,326,359 A | 7/1994 | Oudard |
| 5,330,534 A | 7/1994 | Herrington et al. |
| 5,336,267 A | 8/1994 | Kubein-Meesenburg et al. |
| 5,342,360 A | 8/1994 | Faccioli et al. |
| 5,343,877 A | 9/1994 | Park |
| 5,344,460 A | 9/1994 | Turanyi et al. |
| 5,344,461 A | 9/1994 | Phlipot |
| 5,356,629 A | 10/1994 | Sander et al. |
| 5,358,529 A | 10/1994 | Davidson |
| 5,358,530 A | 10/1994 | Hodorek |
| 5,360,449 A | 11/1994 | Branemark |
| 5,360,451 A | 11/1994 | Keller |
| 5,364,403 A | 11/1994 | Petersen et al. |
| 5,370,692 A | 12/1994 | Fink et al. |
| 5,370,693 A | 12/1994 | Kelman et al. |
| 5,370,698 A | 12/1994 | Heimke et al. |
| 5,370,701 A | 12/1994 | Finn |
| 5,370,702 A | 12/1994 | Jones |
| 5,376,122 A | 12/1994 | Pappas et al. |
| 5,376,123 A | 12/1994 | Klaue et al. |
| 5,376,124 A | 12/1994 | Gustke et al. |
| 5,383,938 A | 1/1995 | Rohr et al. |
| 5,387,239 A | 2/1995 | Bianco et al. |
| 5,387,240 A | 2/1995 | Pottenger et al. |
| 5,387,241 A | 2/1995 | Hayes |
| 5,397,360 A | 3/1995 | Cohen et al. |
| 5,405,392 A | 4/1995 | Deckner |
| 5,405,395 A | 4/1995 | Coates |
| 5,405,400 A | 4/1995 | Linscheid et al. |
| 5,405,401 A | 4/1995 | Lippincott, III et al. |
| 5,405,403 A | 4/1995 | Mikhail |
| 5,405,404 A | 4/1995 | Gardner et al. |
| 5,411,555 A | 5/1995 | Nieder |
| 5,413,605 A | 5/1995 | Ashby et al. |
| 5,413,607 A | 5/1995 | Engelbrecht et al. |
| 5,413,610 A | 5/1995 | Amino et al. |
| 5,417,696 A | 5/1995 | Kashuba et al. |
| 5,425,778 A | 6/1995 | Zichner et al. |
| 5,425,779 A | 6/1995 | Schlosser et al. |
| 5,431,657 A | 7/1995 | Rohr |
| 5,443,512 A | 8/1995 | Parr et al. |
| 5,443,516 A | 8/1995 | Albrektsson et al. |
| 5,447,492 A | 9/1995 | Cartmell et al. |
| 5,458,637 A | 10/1995 | Hayes |
| 5,462,563 A | 10/1995 | Shearer et al. |
| 5,474,560 A | 12/1995 | Rohr, Jr. |
| 5,480,443 A | 1/1996 | Elias |
| 5,480,444 A | 1/1996 | Incavo et al. |
| 5,480,445 A | 1/1996 | Burkinshaw |
| 5,480,446 A | 1/1996 | Goodfellow et al. |
| 5,480,447 A | 1/1996 | Skiba |
| 5,480,448 A | 1/1996 | Mikhail |
| 5,480,451 A | 1/1996 | Grundei et al. |
| 5,480,452 A | 1/1996 | Hofmann et al. |
| 5,486,178 A | 1/1996 | Hodge |
| 5,486,181 A | 1/1996 | Cohen et al. |
| 5,489,311 A | 2/1996 | Cipolletti |
| 5,507,745 A | 4/1996 | Logroscino et al. |
| 5,507,817 A | 4/1996 | Craig et al. |
| 5,507,818 A | 4/1996 | McLaughlin |
| 5,507,820 A | 4/1996 | Pappas |
| 5,507,826 A | 4/1996 | Besselink et al. |
| 5,507,829 A | 4/1996 | Thongpreda et al. |
| 5,507,832 A | 4/1996 | Michielli et al. |
| 5,510,396 A | 4/1996 | Prewett et al. |
| 5,522,902 A | 6/1996 | Yuan et al. |
| 5,527,317 A | 6/1996 | Ashby et al. |
| 5,531,791 A | 7/1996 | Wolfinbarger, Jr. |
| 5,531,793 A | 7/1996 | Kelman et al. |
| 5,534,032 A | 7/1996 | Hodorek |
| 5,540,697 A | 7/1996 | Rehmann et al. |
| 5,549,684 A | 8/1996 | Amino et al. |
| 5,549,685 A | 8/1996 | Hayes |
| 5,549,689 A | 8/1996 | Epstein et al. |
| 5,549,696 A | 8/1996 | Willi |
| 5,549,699 A | 8/1996 | MacMahon et al. |
| 5,549,701 A | 8/1996 | Mikhail |
| 5,549,703 A | 8/1996 | Daigle et al. |
| 5,549,704 A | 8/1996 | Sutter |
| 5,549,706 A | 8/1996 | McCarthy |
| 5,552,454 A | 9/1996 | Kretschmann et al. |
| 5,556,432 A | 9/1996 | Kubein-Meesenburg et al. |
| 5,556,433 A | 9/1996 | Gabriel et al. |
| 5,571,111 A | 11/1996 | Aboczky |
| 5,571,193 A | 11/1996 | Kampner |
| 5,571,194 A | 11/1996 | Gabriel |
| 5,571,196 A | 11/1996 | Stein |
| 5,571,201 A | 11/1996 | Averill et al. |
| 5,571,202 A | 11/1996 | Mathys, Sr. et al. |
| 5,580,352 A | 12/1996 | Sekel |
| 5,584,837 A | 12/1996 | Petersen |
| 5,593,447 A | 1/1997 | Angeli |

(56) References Cited

U.S. PATENT DOCUMENTS

| | | |
|---|---|---|
| 5,593,449 A | 1/1997 | Roberson, Jr. |
| 5,593,450 A | 1/1997 | Scott et al. |
| 5,593,451 A | 1/1997 | Averill et al. |
| 5,609,641 A | 3/1997 | Johnson et al. |
| 5,609,642 A | 3/1997 | Johnson et al. |
| 5,609,645 A | 3/1997 | Vinciguerra |
| 5,609,647 A | 3/1997 | Kalberer et al. |
| 5,609,648 A | 3/1997 | Oehy et al. |
| 5,624,444 A | 4/1997 | Wixon et al. |
| 5,639,280 A | 6/1997 | Warner et al. |
| 5,641,323 A | 6/1997 | Caldarise |
| 5,645,593 A | 7/1997 | Woods et al. |
| 5,645,594 A | 7/1997 | Devanathan et al. |
| 5,645,604 A | 7/1997 | Schneider et al. |
| 5,653,765 A | 8/1997 | McTighe et al. |
| 5,658,294 A | 8/1997 | Sederholm |
| 5,658,344 A | 8/1997 | Hurlburt |
| 5,658,346 A | 8/1997 | Willi |
| 5,658,348 A | 8/1997 | Rohr, Jr. |
| 5,658,349 A | 8/1997 | Brooks et al. |
| 5,662,656 A | 9/1997 | White |
| 5,676,700 A | 10/1997 | Black et al. |
| 5,676,704 A | 10/1997 | Ries et al. |
| 5,681,354 A | 10/1997 | Eckhoff |
| 5,683,399 A | 11/1997 | Jones |
| 5,683,472 A | 11/1997 | O'Neil et al. |
| 5,702,463 A | 12/1997 | Pothier et al. |
| 5,702,475 A | 12/1997 | Zahedi |
| 5,702,476 A | 12/1997 | Limacher et al. |
| 5,702,477 A | 12/1997 | Capello et al. |
| 5,702,478 A | 12/1997 | Tornier |
| 5,702,482 A | 12/1997 | Thongpreda et al. |
| 5,702,487 A | 12/1997 | Averill et al. |
| 5,720,752 A | 2/1998 | Elliott et al. |
| 5,725,589 A | 3/1998 | Pfaff et al. |
| 5,725,591 A | 3/1998 | DeCarlo, Jr. et al. |
| 5,725,597 A | 3/1998 | Hwang |
| 5,735,901 A | 4/1998 | Maumy et al. |
| 5,746,771 A | 5/1998 | Clement, Jr. et al. |
| 5,749,877 A | 5/1998 | Young |
| 5,755,794 A | 5/1998 | Benson |
| 5,755,800 A | 5/1998 | O'Neil et al. |
| 5,755,805 A | 5/1998 | Whiteside |
| 5,755,806 A | 5/1998 | Stalcup et al. |
| 5,755,807 A | 5/1998 | Anstaett et al. |
| 5,755,808 A | 5/1998 | DeCarlo et al. |
| 5,766,255 A | 6/1998 | Slamin et al. |
| 5,766,256 A | 6/1998 | Oudard et al. |
| 5,766,260 A | 6/1998 | Whiteside |
| 5,766,262 A | 6/1998 | Mikhail |
| 5,776,200 A | 7/1998 | Johnson et al. |
| 5,776,201 A | 7/1998 | Colleran et al. |
| 5,776,202 A | 7/1998 | Copf et al. |
| 5,782,920 A | 7/1998 | Colleran |
| 5,782,921 A | 7/1998 | Colleran et al. |
| 5,782,924 A | 7/1998 | Johnson |
| 5,782,925 A | 7/1998 | Collazo et al. |
| 5,782,928 A | 7/1998 | Ries et al. |
| 5,782,930 A | 7/1998 | Lin et al. |
| 5,788,976 A | 8/1998 | Bradford |
| 5,798,924 A | 8/1998 | Eufinger et al. |
| 5,800,554 A | 9/1998 | Scholz |
| 5,800,555 A | 9/1998 | Gray, III |
| 5,800,556 A | 9/1998 | Sanders et al. |
| 5,800,558 A | 9/1998 | LaHaise, Sr. |
| 5,800,560 A | 9/1998 | Draenert |
| 5,817,096 A | 10/1998 | Salyer |
| 5,824,097 A | 10/1998 | Gabriel et al. |
| 5,824,107 A | 10/1998 | Tschirren |
| 5,824,108 A | 10/1998 | Huebner |
| 5,830,215 A | 11/1998 | Incavo et al. |
| 5,858,020 A | 1/1999 | Johnson et al. |
| 5,865,850 A | 2/1999 | Matthews |
| 5,871,547 A | 2/1999 | Abouaf et al. |
| 5,871,548 A | 2/1999 | Sanders et al. |
| 5,876,459 A | 3/1999 | Powell |
| 5,879,387 A | 3/1999 | Jones et al. |
| 5,879,390 A | 3/1999 | Kubein-Meesenburg et al. |
| 5,879,391 A | 3/1999 | Slamin |
| 5,879,398 A | 3/1999 | Swarts et al. |
| 5,879,401 A | 3/1999 | Besemer et al. |
| 5,879,402 A | 3/1999 | Lawes et al. |
| 5,879,404 A | 3/1999 | Bateman et al. |
| 5,879,405 A | 3/1999 | Ries et al. |
| 5,879,406 A | 3/1999 | Lilley |
| 5,888,205 A | 3/1999 | Pratt et al. |
| 5,888,206 A | 3/1999 | Lob et al. |
| 5,888,211 A | 3/1999 | Sanders |
| 5,899,942 A | 5/1999 | Berman |
| 5,902,340 A | 5/1999 | White et al. |
| 5,904,688 A | 5/1999 | Gilbert et al. |
| 5,904,720 A | 5/1999 | Farrar et al. |
| 5,906,644 A | 5/1999 | Powell |
| 5,910,172 A | 6/1999 | Penenberg |
| 5,916,269 A | 6/1999 | Serbousek et al. |
| 5,916,270 A | 6/1999 | Lipman |
| 5,919,236 A | 7/1999 | Pfaff et al. |
| 5,928,286 A | 7/1999 | Ashby et al. |
| 5,928,287 A | 7/1999 | Keller |
| 5,931,870 A | 8/1999 | Cuckler et al. |
| 5,935,171 A | 8/1999 | Schneider et al. |
| 5,935,175 A | 8/1999 | Ostiguy, Jr. et al. |
| 5,938,702 A | 8/1999 | Lopez et al. |
| 5,944,756 A | 8/1999 | Fischetti et al. |
| 5,944,759 A | 8/1999 | Link |
| 5,951,603 A | 9/1999 | O'Neil et al. |
| 5,954,727 A | 9/1999 | Collazo |
| 5,957,979 A | 9/1999 | Beckman et al. |
| 5,961,516 A | 10/1999 | Graf |
| 5,972,368 A | 10/1999 | McKay |
| 5,973,222 A | 10/1999 | Devanathan et al. |
| 5,976,148 A | 11/1999 | Charpenet et al. |
| 5,976,188 A | 11/1999 | Dextradeur et al. |
| 5,976,189 A | 11/1999 | Keller |
| 5,977,204 A | 11/1999 | Boyan et al. |
| 5,980,574 A | 11/1999 | Takei et al. |
| 5,984,968 A | 11/1999 | Park |
| 5,984,969 A | 11/1999 | Matthews et al. |
| 5,989,293 A | 11/1999 | Cook et al. |
| 5,989,294 A | 11/1999 | Marlow |
| 5,997,576 A | 12/1999 | Copf |
| 5,997,577 A | 12/1999 | Herrington et al. |
| 5,997,579 A | 12/1999 | Albrektsson et al. |
| 6,004,353 A | 12/1999 | Masini |
| 6,005,018 A | 12/1999 | Cicierega et al. |
| 6,007,580 A | 12/1999 | Lehto et al. |
| 6,008,432 A | 12/1999 | Taylor |
| 6,010,533 A | 1/2000 | Pope et al. |
| 6,010,534 A | 1/2000 | O'Neil et al. |
| 6,013,080 A | 1/2000 | Khalili |
| 6,013,081 A | 1/2000 | Burkinshaw et al. |
| 6,013,103 A | 1/2000 | Kaufman et al. |
| 6,013,104 A | 1/2000 | Kampner |
| 6,015,937 A | 1/2000 | Br.ang.nemark |
| 6,017,975 A | 1/2000 | Saum et al. |
| 6,027,505 A | 2/2000 | Peter et al. |
| 6,039,764 A | 3/2000 | Pottenger et al. |
| 6,042,611 A | 3/2000 | Noiles |
| 6,045,583 A | 4/2000 | Gross et al. |
| 6,053,945 A | 4/2000 | O'Neil et al. |
| 6,056,779 A | 5/2000 | Noyer et al. |
| 6,059,833 A | 5/2000 | Doets |
| 6,063,091 A | 5/2000 | Lombardo et al. |
| 6,063,124 A | 5/2000 | Amstutz |
| 6,066,176 A | 5/2000 | Oshida |
| 6,071,311 A | 6/2000 | O'Neil et al. |
| 6,074,424 A | 6/2000 | Perrone, Jr. et al. |
| 6,074,425 A | 6/2000 | Pappas |
| 6,080,195 A | 6/2000 | Colleran et al. |
| 6,086,614 A | 7/2000 | Mumme |
| 6,087,553 A | 7/2000 | Cohen et al. |
| 6,090,146 A | 7/2000 | Rozow, III et al. |
| 6,093,208 A | 7/2000 | Tian |
| 6,096,082 A | 8/2000 | Stegmuller et al. |

(56) References Cited

U.S. PATENT DOCUMENTS

| | | |
|---|---|---|
| 6,099,569 A | 8/2000 | Keller |
| 6,099,571 A | 8/2000 | Knapp |
| 6,113,640 A | 9/2000 | Tormala et al. |
| 6,117,175 A | 9/2000 | Bosredon |
| 6,120,543 A | 9/2000 | Kubein-Meesenburg et al. |
| 6,120,545 A | 9/2000 | Hamelijnck et al. |
| 6,126,690 A | 10/2000 | Ateshian et al. |
| 6,126,691 A | 10/2000 | Kasra et al. |
| 6,126,692 A | 10/2000 | Robie et al. |
| 6,126,693 A | 10/2000 | O'Neil et al. |
| 6,126,694 A | 10/2000 | Gray, Jr. |
| 6,126,695 A | 10/2000 | Semlitsch |
| 6,129,765 A | 10/2000 | Lopez et al. |
| 6,132,468 A | 10/2000 | Mansmann |
| 6,132,469 A | 10/2000 | Schroeder |
| 6,136,029 A | 10/2000 | Johnson et al. |
| 6,136,033 A | 10/2000 | Suemer |
| 6,136,035 A | 10/2000 | Lob et al. |
| 6,139,584 A | 10/2000 | Ochoa et al. |
| 6,142,998 A | 11/2000 | Smith et al. |
| 6,143,232 A | 11/2000 | Rohr |
| 6,146,424 A | 11/2000 | Gray, Jr. et al. |
| 6,149,687 A | 11/2000 | Gray, Jr. et al. |
| 6,152,930 A | 11/2000 | Mastrorio |
| 6,152,961 A | 11/2000 | Ostiguy, Jr. et al. |
| 6,156,070 A | 12/2000 | Incavo et al. |
| 6,162,255 A | 12/2000 | Oyola |
| 6,162,256 A | 12/2000 | Ostiguy, Jr. et al. |
| 6,165,220 A | 12/2000 | McKellop et al. |
| 6,165,222 A | 12/2000 | Hoeppner et al. |
| 6,165,223 A | 12/2000 | Metzger et al. |
| 6,168,600 B1 | 1/2001 | Grace et al. |
| 6,171,342 B1 | 1/2001 | O'Neil et al. |
| 6,174,934 B1 | 1/2001 | Sun et al. |
| 6,179,876 B1 | 1/2001 | Stamper et al. |
| 6,179,877 B1 | 1/2001 | Burke |
| 6,193,759 B1 | 2/2001 | Ro et al. |
| 6,197,032 B1 | 3/2001 | Lawes et al. |
| 6,200,324 B1 | 3/2001 | Regni, Jr. |
| 6,206,929 B1 | 3/2001 | Ochoa et al. |
| 6,214,014 B1 | 4/2001 | McGann |
| 6,214,052 B1 | 4/2001 | Burkinshaw |
| 6,214,053 B1 | 4/2001 | Ling et al. |
| 6,217,615 B1 | 4/2001 | Sioshansi et al. |
| 6,217,619 B1 | 4/2001 | Keller |
| 6,221,110 B1 | 4/2001 | Copf |
| 6,224,633 B1 | 5/2001 | Kalberer et al. |
| 6,228,091 B1 | 5/2001 | Lombardo et al. |
| 6,228,121 B1 | 5/2001 | Khalili |
| 6,231,611 B1 | 5/2001 | Mosseri |
| 6,235,060 B1 | 5/2001 | Kubein-Meesenburg et al. |
| 6,245,111 B1 | 6/2001 | Shaffner |
| 6,248,132 B1 | 6/2001 | Harris |
| 6,264,698 B1 | 7/2001 | Lawes et al. |
| 6,264,699 B1 | 7/2001 | Noiles et al. |
| 6,267,785 B1 | 7/2001 | Masini |
| 6,281,264 B1 | 8/2001 | Salovey et al. |
| 6,284,001 B1 | 9/2001 | Knapp |
| 6,290,725 B1 | 9/2001 | Weiss et al. |
| 6,290,726 B1 | 9/2001 | Pope et al. |
| 6,290,727 B1 | 9/2001 | Otto et al. |
| 6,293,971 B1 | 9/2001 | Nelson et al. |
| 6,296,667 B1 | 10/2001 | Johnson et al. |
| 6,302,890 B1 | 10/2001 | Leone, Jr. |
| 6,306,172 B1 | 10/2001 | O'Neil et al. |
| 6,319,285 B1 | 11/2001 | Chamier et al. |
| 6,325,829 B1 | 12/2001 | Schmotzer |
| 6,334,875 B1 | 1/2002 | Keller |
| 6,340,370 B1 | 1/2002 | Willert et al. |
| 6,342,075 B1 | 1/2002 | MacArthur |
| 6,344,060 B1 | 2/2002 | Schmotzer et al. |
| 6,344,496 B1 | 2/2002 | Niederauer et al. |
| 6,352,559 B1 | 3/2002 | Church |
| 6,358,282 B1 | 3/2002 | Wymann |
| 6,361,566 B1 | 3/2002 | Al-Hafez |
| 6,368,354 B2 | 4/2002 | Burstein et al. |
| 6,376,573 B1 | 4/2002 | White et al. |
| 6,379,389 B1 | 4/2002 | Koch |
| 6,383,227 B1 | 5/2002 | Baroud et al. |
| 6,387,131 B1 | 5/2002 | Miehlke et al. |
| 6,391,251 B1 | 5/2002 | Keicher et al. |
| 6,413,279 B1 | 7/2002 | Metzger et al. |
| 6,413,280 B1 | 7/2002 | Feiler |
| 6,416,552 B1 | 7/2002 | Hoeppner et al. |
| 6,423,096 B1 | 7/2002 | Musset et al. |
| 6,425,921 B1 | 7/2002 | Grundei et al. |
| 6,428,578 B2 | 8/2002 | White |
| 6,432,141 B1 | 8/2002 | Stocks et al. |
| 6,436,145 B1 | 8/2002 | Miller |
| 6,436,146 B1 | 8/2002 | Hassler et al. |
| 6,447,549 B1 | 9/2002 | Taft |
| 6,447,550 B1 | 9/2002 | Hunter et al. |
| 6,451,058 B2 | 9/2002 | Tuke et al. |
| 6,468,281 B1 | 10/2002 | Badorf et al. |
| 6,475,243 B1 | 11/2002 | Sheldon et al. |
| 6,482,237 B2 | 11/2002 | Mosseri |
| 6,485,519 B2 | 11/2002 | Meyers et al. |
| 6,488,713 B1 | 12/2002 | Hershberger |
| 6,488,715 B1 | 12/2002 | Pope et al. |
| 6,491,726 B2 | 12/2002 | Pappas |
| 6,494,914 B2 | 12/2002 | Brown et al. |
| 6,497,728 B2 | 12/2002 | Yong |
| 6,500,207 B1 | 12/2002 | Keller |
| 6,500,208 B1 | 12/2002 | Metzger et al. |
| 6,503,281 B1 | 1/2003 | Mallory |
| 6,506,215 B1 | 1/2003 | Letot et al. |
| 6,517,583 B1 | 2/2003 | Pope et al. |
| 6,518,328 B2 | 2/2003 | Kumar |
| 6,520,995 B2 | 2/2003 | Church |
| 6,524,344 B2 | 2/2003 | Yoon |
| 6,524,345 B1 | 2/2003 | Valimaa et al. |
| 6,527,807 B1 | 3/2003 | O'Neil et al. |
| 6,527,808 B1 | 3/2003 | Albertorio et al. |
| 6,527,809 B1 | 3/2003 | Doursounian et al. |
| 6,527,810 B2 | 3/2003 | Johnson et al. |
| 6,537,321 B1 | 3/2003 | Horber |
| 6,540,786 B2 | 4/2003 | Chibrac et al. |
| 6,558,427 B2 | 5/2003 | Leclercq et al. |
| 6,565,575 B2 | 5/2003 | Lewis |
| 6,565,606 B1 | 5/2003 | Bruce et al. |
| 6,589,248 B1 | 7/2003 | Hughes |
| 6,589,283 B1 | 7/2003 | Metzger et al. |
| 6,589,284 B1 | 7/2003 | Silberer |
| 6,602,259 B1 | 8/2003 | Masini |
| 6,605,293 B1 | 8/2003 | Giordano et al. |
| 6,610,097 B2 | 8/2003 | Serbousek et al. |
| 6,613,092 B1 | 9/2003 | Kana et al. |
| 6,616,696 B1 | 9/2003 | Merchant |
| 6,620,198 B2 | 9/2003 | Burstein et al. |
| 6,623,488 B1 | 9/2003 | Leone, Jr. |
| 6,626,950 B2 | 9/2003 | Brown et al. |
| 6,629,999 B1 | 10/2003 | Serafin, Jr. |
| 6,641,617 B1 | 11/2003 | Merrill et al. |
| 6,652,533 B2 | 11/2003 | O'Neil |
| 6,652,586 B2 | 11/2003 | Hunter et al. |
| 6,652,589 B2 | 11/2003 | Schmotzer et al. |
| 6,652,590 B2 | 11/2003 | Zitnansky et al. |
| 6,660,040 B2 | 12/2003 | Chan et al. |
| 6,669,728 B2 | 12/2003 | Despres, III et al. |
| 6,679,890 B2 | 1/2004 | Margulies et al. |
| 6,682,566 B2 | 1/2004 | Draenert |
| 6,682,567 B1 | 1/2004 | Schroeder |
| 6,682,568 B2 | 1/2004 | Despres, III et al. |
| 6,692,531 B1 | 2/2004 | Yoon et al. |
| 6,699,293 B2 | 3/2004 | White |
| 6,706,071 B1 | 3/2004 | Wolter |
| 6,706,072 B2 | 3/2004 | Dwyer et al. |
| 6,712,857 B1 | 3/2004 | Roger |
| 6,712,858 B1 | 3/2004 | Grundei et al. |
| 6,716,248 B2 | 4/2004 | Huene |
| 6,719,800 B2 | 4/2004 | Meyers et al. |
| 6,723,129 B2 | 4/2004 | Dwyer et al. |
| 6,726,725 B2 | 4/2004 | Hunter et al. |
| 6,740,092 B2 | 5/2004 | Lombardo et al. |

(56) References Cited

U.S. PATENT DOCUMENTS

| | | |
|---|---|---|
| 6,743,258 B1 | 6/2004 | Keller |
| 6,755,864 B1 | 6/2004 | Brack et al. |
| 6,758,864 B2 | 7/2004 | Storer et al. |
| 6,761,741 B2 | 7/2004 | Iesaka |
| 6,764,516 B2 | 7/2004 | Pappas |
| 6,770,097 B2 | 8/2004 | Leclercq |
| 6,773,461 B2 | 8/2004 | Meyers et al. |
| 6,783,550 B2 | 8/2004 | MacArthur |
| 6,786,933 B2 | 9/2004 | Merrill et al. |
| 6,793,681 B1 | 9/2004 | Pope et al. |
| 6,800,670 B2 | 10/2004 | Shen et al. |
| 6,802,866 B2 | 10/2004 | Bunz |
| 6,811,568 B2 | 11/2004 | Minamikawa |
| 6,811,569 B1 | 11/2004 | Afriat et al. |
| 6,818,019 B2 | 11/2004 | Horber |
| 6,818,020 B2 | 11/2004 | Sun et al. |
| 6,827,739 B2 | 12/2004 | Griner et al. |
| 6,827,742 B2 | 12/2004 | Hayes, Jr. et al. |
| 6,840,944 B2 | 1/2005 | Suddaby |
| 6,843,805 B2 | 1/2005 | Webb et al. |
| 6,843,806 B2 | 1/2005 | Hayes, Jr. et al. |
| 6,863,692 B2 | 3/2005 | Meulink |
| 6,866,683 B2 | 3/2005 | Gerbec et al. |
| 6,866,685 B2 | 3/2005 | Chan et al. |
| 6,869,447 B2 | 3/2005 | Lee et al. |
| 6,875,237 B2 | 4/2005 | Dye |
| 6,881,229 B2 | 4/2005 | Khandkar et al. |
| 6,887,276 B2 | 5/2005 | Gerbec et al. |
| 6,896,702 B2 | 5/2005 | Collazo |
| 6,905,515 B1 | 6/2005 | Gilbertson |
| 6,908,486 B2 | 6/2005 | Lewallen |
| 6,916,340 B2 | 7/2005 | Metzger et al. |
| 6,916,341 B2 | 7/2005 | Rolston |
| 6,923,833 B2 | 8/2005 | Wasielewski |
| 6,926,738 B2 | 8/2005 | Wyss |
| 6,926,739 B1 | 8/2005 | O'Connor et al. |
| 6,926,740 B2 | 8/2005 | Lewis et al. |
| 6,944,518 B2 | 9/2005 | Roose |
| 6,953,479 B2 | 10/2005 | Carson et al. |
| 6,962,607 B2 | 11/2005 | Gundlapalli et al. |
| 6,966,932 B1 | 11/2005 | Schroeder |
| 6,969,406 B2 | 11/2005 | Tornier |
| 6,972,021 B2 | 12/2005 | Raugel |
| 6,972,039 B2 | 12/2005 | Metzger et al. |
| 6,981,991 B2 | 1/2006 | Ferree |
| 6,986,791 B1 | 1/2006 | Metzger |
| 7,004,946 B2 | 2/2006 | Parker et al. |
| 7,022,142 B2 | 4/2006 | Johnson |
| 7,025,788 B2 | 4/2006 | Metzger et al. |
| 7,037,310 B2 | 5/2006 | Murphy |
| 7,044,974 B2 | 5/2006 | Garber et al. |
| 7,051,417 B2 | 5/2006 | Michelson |
| 7,056,577 B1 | 6/2006 | Bruce et al. |
| 7,070,622 B1 | 7/2006 | Brown et al. |
| 7,074,241 B2 | 7/2006 | McKinnon |
| 7,105,026 B2 | 9/2006 | Johnson et al. |
| 7,108,719 B2 | 9/2006 | Horber |
| 7,125,193 B2 | 10/2006 | Despres, III et al. |
| 7,131,995 B2 | 11/2006 | Biedermann et al. |
| 7,153,326 B1 | 12/2006 | Metzger |
| 7,156,880 B2 | 1/2007 | Evans et al. |
| 7,166,133 B2 | 1/2007 | Evans et al. |
| 7,179,295 B2 | 2/2007 | Kovacevic |
| 7,189,263 B2 | 3/2007 | Erbe et al. |
| 7,192,448 B2 | 3/2007 | Ferree |
| 7,198,642 B2 | 4/2007 | Hazebrouck et al. |
| 7,445,639 B2 | 11/2008 | Metzger et al. |
| 7,497,874 B1 | 3/2009 | Metzger et al. |
| 8,157,869 B2 | 4/2012 | Metzger et al. |
| 8,163,028 B2 | 4/2012 | Metzger et al. |
| 8,187,280 B2 | 5/2012 | May et al. |
| 8,328,873 B2 | 12/2012 | Metzger et al. |
| 2001/0014828 A1 | 8/2001 | Yoon |
| 2001/0014829 A1 | 8/2001 | Yoon |
| 2001/0016780 A1 | 8/2001 | Yong San |
| 2001/0018616 A1 | 8/2001 | Schwab |
| 2001/0032021 A1 | 10/2001 | McKinnon |
| 2001/0037156 A1 | 11/2001 | Burstein et al. |
| 2001/0039456 A1 | 11/2001 | Boyer et al. |
| 2001/0039457 A1 | 11/2001 | Boyer et al. |
| 2001/0041941 A1 | 11/2001 | Boyer et al. |
| 2001/0051830 A1 | 12/2001 | Tuke et al. |
| 2002/0007294 A1 | 1/2002 | Bradbury et al. |
| 2002/0022889 A1 | 2/2002 | Chibrac et al. |
| 2002/0022890 A1 | 2/2002 | Jacobsson et al. |
| 2002/0040244 A1 | 4/2002 | Despres et al. |
| 2002/0040245 A1 | 4/2002 | Lester et al. |
| 2002/0042656 A1 | 4/2002 | Hunter et al. |
| 2002/0045949 A1 | 4/2002 | Ling et al. |
| 2002/0049500 A1 | 4/2002 | Draenert |
| 2002/0052659 A1 | 5/2002 | Hayes et al. |
| 2002/0059000 A1 | 5/2002 | Dwyer et al. |
| 2002/0068980 A1 | 6/2002 | Serbousek et al. |
| 2002/0072799 A1 | 6/2002 | Despres et al. |
| 2002/0082706 A1 | 6/2002 | Raugel |
| 2002/0107577 A1 | 8/2002 | Storer et al. |
| 2002/0116007 A1 | 8/2002 | Lewis |
| 2002/0116068 A1 | 8/2002 | McLean |
| 2002/0120340 A1 | 8/2002 | Metzger et al. |
| 2002/0120341 A1 | 8/2002 | Stumpo et al. |
| 2002/0128653 A1 | 9/2002 | Haidukewych |
| 2002/0138148 A1 | 9/2002 | Hyde |
| 2002/0138151 A1 | 9/2002 | Hubbard et al. |
| 2002/0139818 A1 | 10/2002 | McGuffey |
| 2002/0143402 A1 | 10/2002 | Steinberg |
| 2002/0143403 A1 | 10/2002 | Vaidyanathan et al. |
| 2002/0151978 A1 | 10/2002 | Zacouto et al. |
| 2002/0156536 A1 | 10/2002 | Harris et al. |
| 2002/0165615 A1 | 11/2002 | Abouaf et al. |
| 2002/0173853 A1 | 11/2002 | Corl et al. |
| 2003/0009232 A1 | 1/2003 | Metzger et al. |
| 2003/0009234 A1 | 1/2003 | Treacy et al. |
| 2003/0014120 A1 | 1/2003 | Carson et al. |
| 2003/0022069 A1 | 1/2003 | Karube et al. |
| 2003/0033018 A1 | 2/2003 | Merchant |
| 2003/0040805 A1 | 2/2003 | Minamikawa |
| 2003/0050645 A1 | 3/2003 | Parker et al. |
| 2003/0050703 A1 | 3/2003 | Harris et al. |
| 2003/0050705 A1 | 3/2003 | Cueille et al. |
| 2003/0055508 A1 | 3/2003 | Metzger et al. |
| 2003/0055509 A1 | 3/2003 | McCue et al. |
| 2003/0060889 A1 | 3/2003 | Tarabishy |
| 2003/0060890 A1 | 3/2003 | Tarabishy |
| 2003/0065397 A1 | 4/2003 | Hanssen et al. |
| 2003/0074078 A1 | 4/2003 | Doubler et al. |
| 2003/0093156 A1 | 5/2003 | Metzger et al. |
| 2003/0105529 A1 | 6/2003 | Synder et al. |
| 2003/0109933 A1 | 6/2003 | Weissman et al. |
| 2003/0114934 A1 | 6/2003 | Steinberg |
| 2003/0114935 A1 | 6/2003 | Chan et al. |
| 2003/0120346 A1 | 6/2003 | Mercinek et al. |
| 2003/0120347 A1 | 6/2003 | Steinberg |
| 2003/0125810 A1 | 7/2003 | Sullivan et al. |
| 2003/0130740 A1 | 7/2003 | Stocks et al. |
| 2003/0139818 A1 | 7/2003 | Rogers et al. |
| 2003/0149485 A1 | 8/2003 | Tornier |
| 2003/0153981 A1 | 8/2003 | Wang et al. |
| 2003/0153982 A1 | 8/2003 | Pria |
| 2003/0158606 A1 | 8/2003 | Coon et al. |
| 2003/0163202 A1 | 8/2003 | Lakin |
| 2003/0171815 A1 | 9/2003 | Kana et al. |
| 2003/0171817 A1 | 9/2003 | Rambert et al. |
| 2003/0181984 A1 | 9/2003 | Abendschein |
| 2003/0181987 A1 | 9/2003 | Muirhead-Allwood |
| 2003/0204262 A1 | 10/2003 | Ferguson et al. |
| 2003/0204263 A1 | 10/2003 | Justin et al. |
| 2003/0204268 A1 | 10/2003 | Gerbec et al. |
| 2003/0204269 A1 | 10/2003 | Gerbec et al. |
| 2003/0208276 A1 | 11/2003 | Berelsman et al. |
| 2003/0212458 A1 | 11/2003 | Harris et al. |
| 2003/0220697 A1 | 11/2003 | Justin et al. |
| 2003/0220699 A1 | 11/2003 | Hunter et al. |
| 2003/0225457 A1 | 12/2003 | Justin et al. |
| 2003/0225458 A1 | 12/2003 | Donkers et al. |

(56) References Cited

U.S. PATENT DOCUMENTS

| | | |
|---|---|---|
| 2003/0229356 A1 | 12/2003 | Dye |
| 2003/0229398 A1 | 12/2003 | Iesaka |
| 2004/0002766 A1 | 1/2004 | Hunter et al. |
| 2004/0019380 A1 | 1/2004 | Baege et al. |
| 2004/0019382 A1 | 1/2004 | Amirouche et al. |
| 2004/0019386 A1 | 1/2004 | Ferree |
| 2004/0024460 A1 | 2/2004 | Ferree |
| 2004/0030344 A1 | 2/2004 | Dye et al. |
| 2004/0030394 A1 | 2/2004 | Horber |
| 2004/0030400 A1 | 2/2004 | Horber |
| 2004/0034432 A1 | 2/2004 | Hughes et al. |
| 2004/0039449 A1 | 2/2004 | Tornier |
| 2004/0039451 A1 | 2/2004 | Southworth |
| 2004/0049284 A1 | 3/2004 | German et al. |
| 2004/0049285 A1 | 3/2004 | Haas |
| 2004/0049286 A1 | 3/2004 | German et al. |
| 2004/0054418 A1 | 3/2004 | McLean et al. |
| 2004/0059427 A1 | 3/2004 | Serbousek et al. |
| 2004/0068324 A1 | 4/2004 | Grundei |
| 2004/0073226 A1 | 4/2004 | Cotting et al. |
| 2004/0073315 A1 | 4/2004 | Justin et al. |
| 2004/0078083 A1 | 4/2004 | Gibbs et al. |
| 2004/0083004 A1 | 4/2004 | Wasielewski |
| 2004/0098133 A1 | 5/2004 | Carignan et al. |
| 2004/0098134 A1 | 5/2004 | Meulink |
| 2004/0102851 A1 | 5/2004 | Saladino |
| 2004/0102852 A1 | 5/2004 | Johnson et al. |
| 2004/0107594 A1 | 6/2004 | Afriat |
| 2004/0117023 A1 | 6/2004 | Gerbec et al. |
| 2004/0117024 A1 | 6/2004 | Gerbec et al. |
| 2004/0117029 A1 | 6/2004 | Lewis et al. |
| 2004/0122521 A1 | 6/2004 | Lee et al. |
| 2004/0122524 A1 | 6/2004 | Hunter et al. |
| 2004/0143336 A1 | 7/2004 | Burkinshaw |
| 2004/0143341 A1 | 7/2004 | McLean |
| 2004/0147926 A1 | 7/2004 | Iversen |
| 2004/0153063 A1 | 8/2004 | Harris |
| 2004/0162619 A1 | 8/2004 | Blaylock et al. |
| 2004/0162620 A1 | 8/2004 | Wyss |
| 2004/0162621 A1 | 8/2004 | Crofford |
| 2004/0172137 A1 | 9/2004 | Blaylock et al. |
| 2004/0172139 A1 | 9/2004 | Dwyer et al. |
| 2004/0186580 A1 | 9/2004 | Steinmann |
| 2004/0186586 A1 | 9/2004 | Seyer et al. |
| 2004/0193282 A1 | 9/2004 | Hanes |
| 2004/0199257 A1 | 10/2004 | Dooney |
| 2004/0199259 A1 | 10/2004 | Pichon et al. |
| 2004/0204760 A1 | 10/2004 | Fitz et al. |
| 2004/0204767 A1 | 10/2004 | Park et al. |
| 2004/0210316 A1 | 10/2004 | King et al. |
| 2004/0225368 A1 | 11/2004 | Plumet et al. |
| 2004/0225370 A1 | 11/2004 | Cruchet et al. |
| 2004/0225371 A1 | 11/2004 | Roger |
| 2004/0226343 A1 | 11/2004 | Babler et al. |
| 2004/0236428 A1 | 11/2004 | Burkinshaw et al. |
| 2004/0243249 A1 | 12/2004 | Ishihara et al. |
| 2004/0255749 A1 | 12/2004 | Hayden |
| 2004/0260396 A1 | 12/2004 | Ferree et al. |
| 2004/0267374 A1 | 12/2004 | Friedrichs |
| 2004/0267375 A1 | 12/2004 | Friedrichs |
| 2005/0004677 A1 | 1/2005 | Johnson |
| 2005/0004678 A1 | 1/2005 | Richards |
| 2005/0010288 A1 | 1/2005 | Merrill et al. |
| 2005/0010303 A1 | 1/2005 | Nogier |
| 2005/0010304 A1 | 1/2005 | Jamali |
| 2005/0021149 A1 | 1/2005 | Borruto et al. |
| 2005/0027302 A1 | 2/2005 | Cueille et al. |
| 2005/0033442 A1 | 2/2005 | Fisher et al. |
| 2005/0033445 A1 | 2/2005 | Siebel |
| 2005/0038443 A1 | 2/2005 | Hedley et al. |
| 2005/0043807 A1 | 2/2005 | Wood |
| 2005/0043812 A1 | 2/2005 | Corl et al. |
| 2005/0049524 A1 | 3/2005 | Lefevre et al. |
| 2005/0049713 A1 | 3/2005 | Garber et al. |
| 2005/0055102 A1 | 3/2005 | Tornier et al. |
| 2005/0059972 A1 | 3/2005 | Biscup |
| 2005/0060040 A1 | 3/2005 | Auxepaules et al. |
| 2005/0071014 A1 | 3/2005 | Barnett et al. |
| 2005/0071015 A1 | 3/2005 | Sekel |
| 2005/0075641 A1 | 4/2005 | Singhatat et al. |
| 2005/0080490 A1 | 4/2005 | Bertram |
| 2005/0085823 A1 | 4/2005 | Murphy |
| 2005/0090903 A1 | 4/2005 | Khandkar et al. |
| 2005/0102032 A1 | 5/2005 | Beynnon et al. |
| 2005/0102033 A1 | 5/2005 | Lambert et al. |
| 2005/0102034 A1 | 5/2005 | E. Hayes et al. |
| 2005/0102038 A1 | 5/2005 | Grundei |
| 2005/0107884 A1 | 5/2005 | Johnson et al. |
| 2005/0119755 A1 | 6/2005 | Kristensen |
| 2005/0125067 A1 | 6/2005 | Sweeney |
| 2005/0131540 A1 | 6/2005 | Trieu |
| 2005/0137603 A1 | 6/2005 | Belew et al. |
| 2005/0137708 A1 | 6/2005 | Clark |
| 2005/0137711 A1 | 6/2005 | Southworth et al. |
| 2005/0143828 A1 | 6/2005 | Collins et al. |
| 2005/0143835 A1 | 6/2005 | Gilbertson |
| 2005/0143836 A1 | 6/2005 | Steinberg |
| 2005/0149043 A1 | 7/2005 | Parry et al. |
| 2005/0149047 A1 | 7/2005 | Parry et al. |
| 2005/0154470 A1 | 7/2005 | Sekel |
| 2005/0154471 A1 | 7/2005 | Aram et al. |
| 2005/0165490 A1 | 7/2005 | Tornier |
| 2005/0165491 A1 | 7/2005 | Diaz |
| 2005/0165492 A1 | 7/2005 | Fitz |
| 2005/0171612 A1 | 8/2005 | Rolston |
| 2005/0177172 A1 | 8/2005 | Acker et al. |
| 2005/0177242 A1 | 8/2005 | Lotke |
| 2005/0177244 A1 | 8/2005 | Steinberg |
| 2005/0187635 A1 | 8/2005 | Metzger |
| 2005/0187637 A1 | 8/2005 | Karrer et al. |
| 2005/0192675 A1 | 9/2005 | Robinson |
| 2005/0202371 A1 | 9/2005 | McGuire |
| 2005/0203535 A1 | 9/2005 | Parry et al. |
| 2005/0203629 A1 | 9/2005 | Cipolletti et al. |
| 2005/0209604 A1 | 9/2005 | Penenberg et al. |
| 2005/0211562 A1 | 9/2005 | Rowe et al. |
| 2005/0216091 A1 | 9/2005 | Wasielewski |
| 2005/0228394 A1 | 10/2005 | Bihary et al. |
| 2005/0228395 A1 | 10/2005 | Auxepaules et al. |
| 2005/0228502 A1 | 10/2005 | Deloge et al. |
| 2005/0228503 A1 | 10/2005 | Gundolf |
| 2005/0240275 A1 | 10/2005 | Chappuis |
| 2005/0240276 A1 | 10/2005 | Shea et al. |
| 2005/0246026 A1 | 11/2005 | Lewis et al. |
| 2005/0246027 A1 | 11/2005 | Metzger et al. |
| 2005/0246028 A1 | 11/2005 | Pappas et al. |
| 2005/0246030 A1 | 11/2005 | Yao |
| 2005/0256576 A1 | 11/2005 | Moskowitz et al. |
| 2005/0256584 A1 | 11/2005 | Farrar |
| 2005/0261776 A1 | 11/2005 | Taylor |
| 2005/0267584 A1 | 12/2005 | Burdulis et al. |
| 2005/0267585 A1 | 12/2005 | Sidebotham |
| 2005/0267590 A1 | 12/2005 | Lee |
| 2005/0278034 A1 | 12/2005 | Johnson et al. |
| 2005/0283252 A1 | 12/2005 | Coon et al. |
| 2005/0283253 A1 | 12/2005 | Coon et al. |
| 2005/0283254 A1 | 12/2005 | Hayes et al. |
| 2005/0288791 A1 | 12/2005 | Tornier et al. |
| 2005/0288793 A1 | 12/2005 | Dong et al. |
| 2006/0004463 A1 | 1/2006 | Lewis et al. |
| 2006/0009774 A1 | 1/2006 | Goble et al. |
| 2006/0009853 A1 | 1/2006 | Justin et al. |
| 2006/0009854 A1 | 1/2006 | Justin et al. |
| 2006/0009855 A1 | 1/2006 | Goble et al. |
| 2006/0009857 A1 | 1/2006 | Gibbs et al. |
| 2006/0015188 A1 | 1/2006 | Grimes |
| 2006/0030945 A1 | 2/2006 | Wright |
| 2006/0052876 A1 | 3/2006 | Wozencroft et al. |
| 2006/0058883 A1 | 3/2006 | Aram et al. |
| 2006/0058884 A1 | 3/2006 | Aram et al. |
| 2006/0058886 A1 | 3/2006 | Wozencroft |
| 2006/0064169 A1 | 3/2006 | Ferree |
| 2006/0074491 A1 | 4/2006 | Smith et al. |
| 2006/0085079 A1 | 4/2006 | Carroll |

(56) References Cited

U.S. PATENT DOCUMENTS

| | | |
|---|---|---|
| 2006/0100714 A1 | 5/2006 | Ensign |
| 2006/0129247 A1 | 6/2006 | Brown et al. |
| 2006/0142865 A1 | 6/2006 | Hyde |
| 2006/0142867 A1 | 6/2006 | Metzger et al. |
| 2006/0149285 A1 | 7/2006 | Burgi et al. |
| 2006/0167462 A1 | 7/2006 | Raugel et al. |
| 2006/0167554 A1 | 7/2006 | Heck et al. |
| 2006/0167556 A1 | 7/2006 | Lazennec et al. |
| 2006/0167557 A1 | 7/2006 | Terrill |
| 2006/0167559 A1 | 7/2006 | Johnstone et al. |
| 2006/0167560 A1 | 7/2006 | Heck et al. |
| 2006/0173547 A1 | 8/2006 | Ensign |
| 2006/0173548 A1 | 8/2006 | Auxepaules et al. |
| 2006/0178749 A1 | 8/2006 | Pendleton et al. |
| 2006/0178750 A1 | 8/2006 | Chieng |
| 2006/0184249 A1 | 8/2006 | Tarabishy |
| 2006/0190086 A1 | 8/2006 | Clemow et al. |
| 2006/0195196 A1 | 8/2006 | Pendleton et al. |
| 2006/0206210 A1 | 9/2006 | Abicht et al. |
| 2006/0229734 A1 | 10/2006 | Yoon |
| 2006/0235538 A1 | 10/2006 | Rochetin et al. |
| 2006/0241776 A1 | 10/2006 | Brown et al. |
| 2006/0241781 A1 | 10/2006 | Brown et al. |
| 2006/0265079 A1 | 11/2006 | D'Alessio |
| 2007/0010890 A1 | 1/2007 | Collazo |
| 2007/0021838 A1 | 1/2007 | Dugas et al. |
| 2007/0088443 A1 | 4/2007 | Hanssen et al. |
| 2007/0129809 A1 | 6/2007 | Meridew et al. |
| 2007/0173948 A1 | 7/2007 | Meridew et al. |
| 2007/0196230 A1 | 8/2007 | Hamman et al. |
| 2008/0167722 A1 | 7/2008 | Metzger et al. |
| 2009/0062806 A1 | 3/2009 | Scott et al. |
| 2009/0125114 A1 | 5/2009 | May et al. |
| 2009/0149964 A1 | 6/2009 | May et al. |
| 2009/0299482 A1 | 12/2009 | Metzger et al. |
| 2010/0174378 A1 | 7/2010 | Metzger et al. |
| 2012/0296438 A1 | 11/2012 | Metzger et al. |

FOREIGN PATENT DOCUMENTS

| | | |
|---|---|---|
| EP | 0378928 A1 | 7/1990 |
| EP | 0538987 A1 | 4/1993 |
| EP | 0555003 A1 | 8/1993 |
| EP | 0689796 A1 | 1/1996 |
| EP | 0797417 A1 | 10/1997 |
| EP | 853930 A2 | 7/1998 |
| EP | 0947181 A2 | 10/1999 |
| EP | 0985386 A2 | 3/2000 |
| EP | 993813 A2 | 4/2000 |
| EP | 01004283 A2 | 5/2000 |
| EP | 1398007 A2 | 3/2004 |
| EP | 1430856 A1 | 6/2004 |
| FR | 2718953 A1 | 10/1995 |
| FR | 2793677 A1 | 11/2000 |
| GB | 1553836 A | 10/1979 |
| GB | 2223172 A | 4/1990 |
| JP | 58141847 A | 8/1983 |
| JP | 2001170065 A | 6/2001 |
| JP | 2006237941 A | 9/2006 |
| WO | WO-9613233 A1 | 5/1996 |
| WO | WO-0038598 A1 | 7/2000 |
| WO | WO-0205732 A1 | 1/2002 |
| WO | WO-03065939 A1 | 8/2003 |
| WO | WO-2004078069 A2 | 9/2004 |
| WO | WO-2004080340 A2 | 9/2004 |
| WO | WO-2008118247 A1 | 10/2008 |
| WO | WO-2009049182 A1 | 4/2009 |
| WO | WO-2011017421 A2 | 2/2011 |

OTHER PUBLICATIONS

"AGC Total Knee System, Tradition™ Series," brochure, (11 pages) 1995. Biomet Orthopedics, Inc.

"Ascent™ Total Knee System, Revision Surgical Technique," (pp. 1-24) 2001. Biomet Orthopedics, Inc.

"Finn® Knee System Modularity and Surgical Latitude, Product Ordering Information," catalog, (4 pages) 1994. Biomet, Inc.

"Finn® Knee System Modularity and Surgical Latitude," brochure (pp. 1-20) 1995 Biomet, Inc.

"Finn® Knee System Modularity and Surgical Latitude," brochure, (11 pages) 1990. Biomet, Inc.

"Kinemax® Plus Total Stabiliser (TS) Revision Surgical technique, Xcelerate Instrumentation," brochure/catalog. Stryker Howmedica Osteonics (Dated at least as early as Apr. 4, 2005.).

"OSS™ Orthopaedic Salvage System, Femoral/Tibial Augmentation," brochure, pp. 1-9. 2003, 2004 Biomet Orthopedics, Inc.

"Passport™ Revision Instrumentation, Howmedica Osteonics Total Knee Revision System Surgical Protocol," brochure, Jun. 2000 (pp. 1-27) Stryer® Howmedica Osteonics.

"S-Rom Total Hip System Surgical Technique," (19 pages) located at http://www.rpa.spot.pt/Main-Sections/Informacao-ao-Profissional-de-Saude.aspx?lang=en-GB, web site copyrighted 2008; accessed Oct. 13, 2010. DePuy.

"S-Rom Total Hip System Surgical Technique," brochure (17 pages) 2000. DePuy Orthopaedics, Inc.

"The RHK™ System, RHK™ controlled rotation," brochure (2 sheets) 2004. ArCom™ Biomet Europe.

"Vanguard Complete Knee System, Cruciate Retaining," brochure (6 pages) 2007. Biomet Orthopedics, Inc.

"Vanguard Complete Knee System, System Summary," brochure, (4 sheets) 2007. Biomet Orthopedics, Inc.

Chinese Second Office Action mailed Feb. 4, 2013 for Chinese Application No. 200880111225.7.

European Search Report for EP 02 25 1274 completed on Sep. 12, 2003 (mailed on Sep. 22, 2003).

International Preliminary Report on Patentability and Written Opinion issued Jul. 14, 2009 for PCT/US2008/000374 claiming benefit of U.S. Appl. No. 60/879,733, filed Jan. 10, 2007; and U.S. Appl. No. 60/978,949, filed Oct. 10, 2007.

International Preliminary Report on Patentability for PCT/US2008/079545 issued Apr. 13, 2010, claiming priority to U.S. Appl. No. 60/978,949, filed Oct. 10, 2007.

International Preliminary Report on Patentability for PCT/US2010/044395 mailed Feb. 16, 2012 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.

International Search Report and Written Opinion for PCT/US2008/000374 mailed Jun. 6, 2008.

International Search Report and Written Opinion for PCT/US2008/079545 mailed Jan. 14, 2009 claiming priority to U.S. Appl. No. 60/978,949, filed Oct. 10, 2007.

International Search Report and Written Opinion mailed Jan. 25, 2011 for PCT/US2010/044395 Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of U.S. Appl. No. 11/972,359, filed Jan. 10, 2008; which claims benefit of CIP of U.S. Appl. No. 12/248,509, filed Oct. 9, 2008.

Invitation to Pay Additional Fees mailed Oct. 15, 2010 for PCT/US2010/044395 which claims benefit of U.S. Appl. No. 12/729,852, filed Mar. 23, 2010; which claims benefit of CIP of U.S. Appl. No. 12/536,056, filed Aug. 5, 2009; which claims benefit of CIP of U.S. Appl. No. 12/248,517, filed Oct. 9, 2008; which claims benefit of CIP of 11/972,359, filed Jan. 10, 2008; which claims benefit of CIP of U.S. Appl. No. 12/248,509, filed Oct. 9, 2008.

Japan Office Action mailed Aug. 27, 2013 for Japan Application No. 2010-529093.

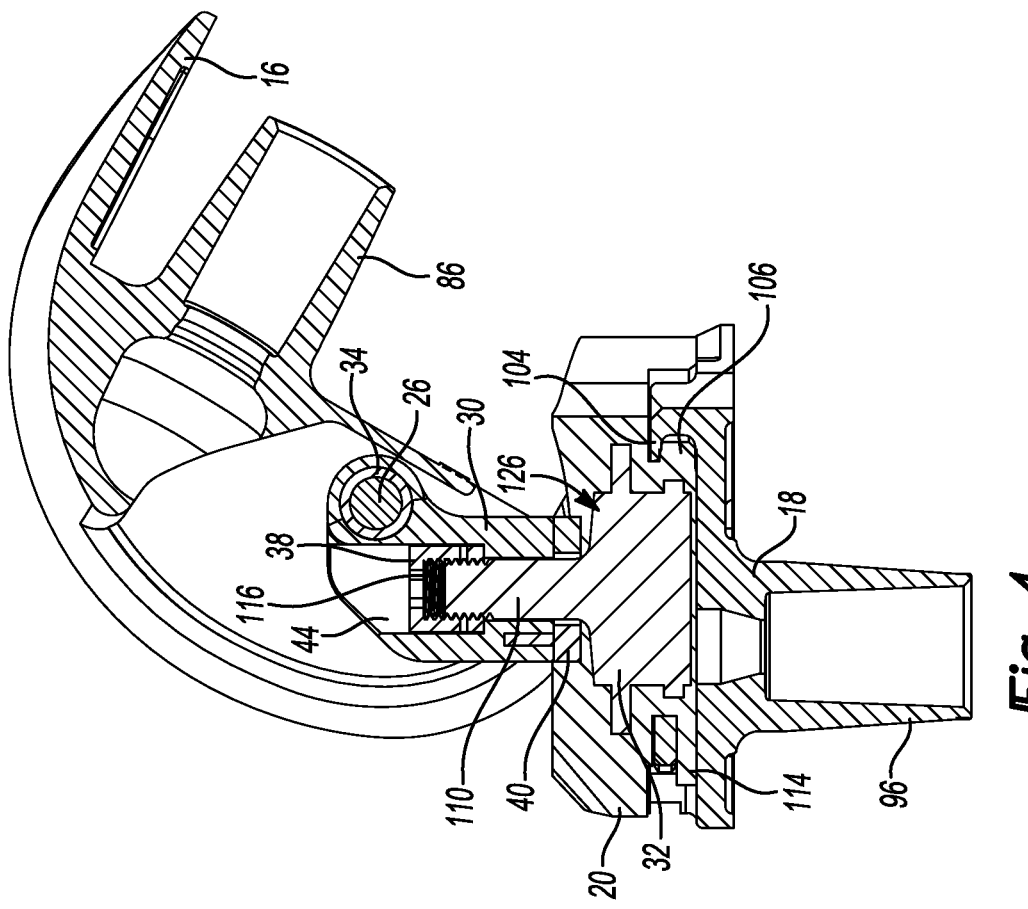
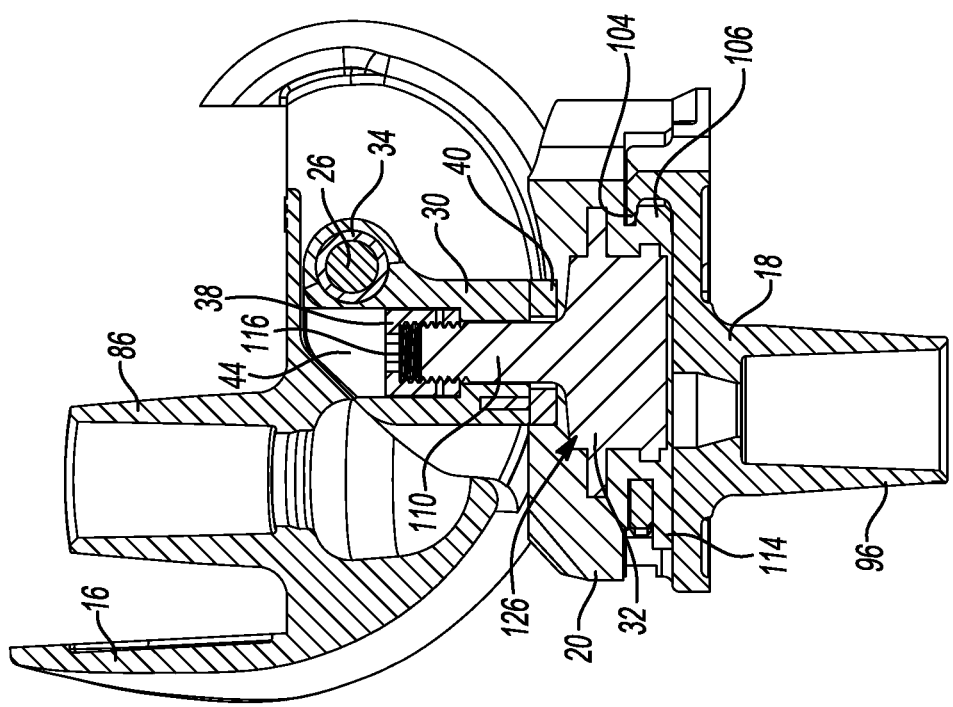

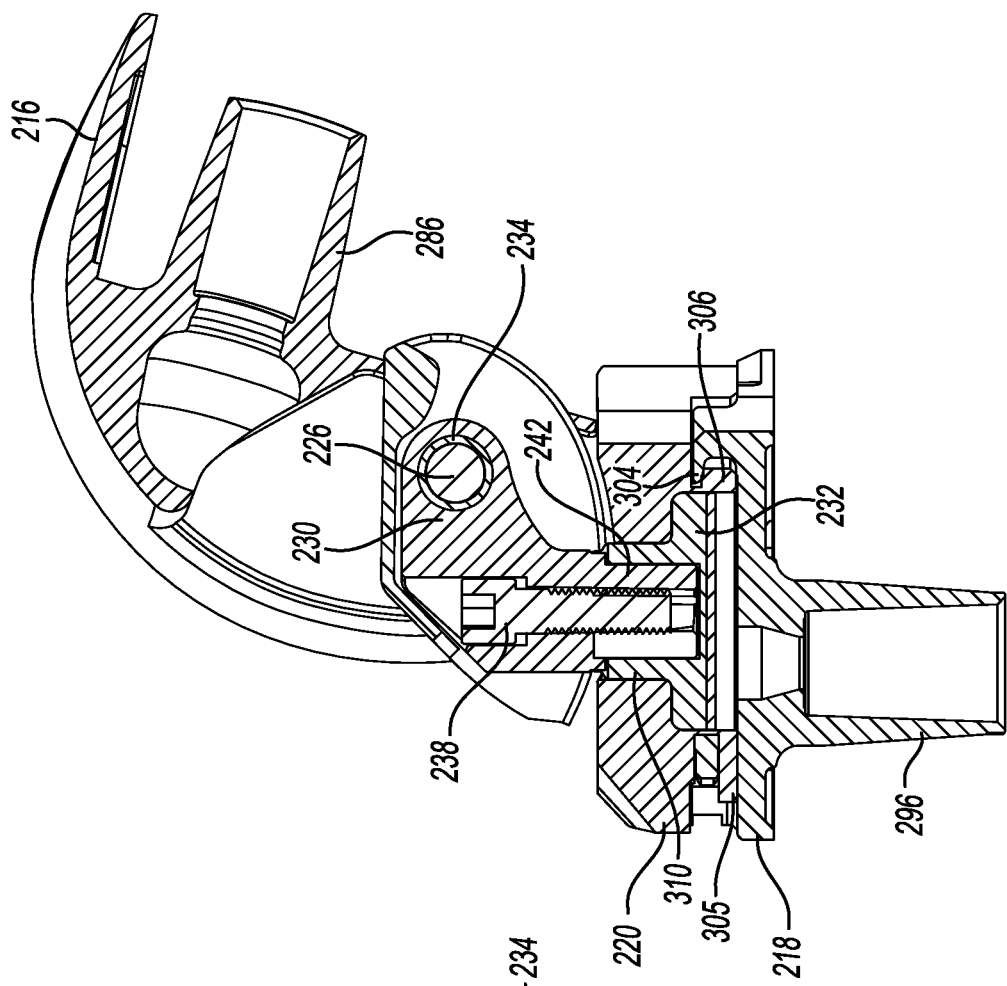
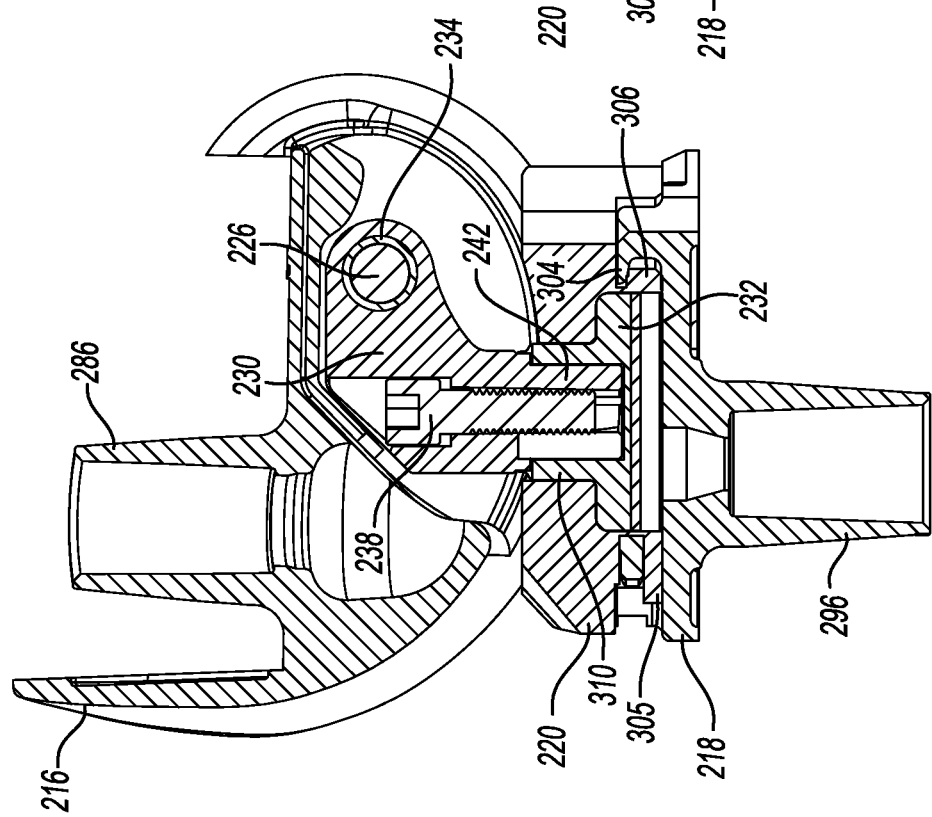

KNEE JOINT PROSTHESIS SYSTEM AND METHOD FOR IMPLANTATION

CROSS-REFERENCE TO RELATED APPLICATIONS

This application is a continuation-in-part of U.S. patent application Ser. No. 13/564,848 filed Aug. 2, 2012, which is a continuation of U.S. patent application Ser. No. 12/729,852 filed Mar. 23, 2010, now U.S. Pat. No. 8,328,873 issued Dec. 11, 2012, which is a continuation-in-part of U.S. patent application Ser. No. 12/536,056 filed Aug. 5, 2009, now U.S. Pat. No. 8,163,028 issued Apr. 24, 2012, which is a continuation-in-part of U.S. patent application Ser. No. 11/972,359 filed Jan. 10, 2008, now U.S. Pat. No. 8,157,869 issued Apr. 17, 2012, which claims priority to U.S. Provisional Application No. 60/978,949, filed Oct. 10, 2007 and U.S. Provisional Application No. 60/879,733 filed Jan. 10, 2007. The entire disclosures of each of the above applications are incorporated herein by reference.

FIELD

The present disclosure relates to knee joint prosthesis and more particularly to a hinged knee joint prosthesis and a method of assembling and implanting the same.

BACKGROUND

A knee joint prosthesis typically comprises a femoral component and a tibial component. The femoral component and tibial component are designed to be surgically attached to the distal end of the femur and the proximal end of the tibia, respectively. The femoral component is further designed to cooperate with the tibial component in simulating the articulating motion of an anatomical knee joint. Such knee joint prostheses are generally referred to as primary knee prostheses.

Knee joint prostheses, in combination with ligaments and muscles, attempt to duplicate natural knee motion as well as absorb and control forces generated during the range of flexion. In some instances however, it may be necessary to replace an existing prosthesis. Such replacement prostheses are generally referred to as revision knee prostheses. In some instances, the primary knee prosthesis, knee tendons and ligaments may become damaged or deteriorated. In this regard, it may be necessary for a revision knee joint prosthesis to eliminate one or more of these motions in order to provide adequate stability. In this way, it may be desirable to provide a cruciate retaining (CR) revision knee, a fully constrained revision knee, a posterior stabilized (PS) revision knee or a hinged revision knee for example. Furthermore, in some instances it may be necessary to account for bone loss in areas adjacent to such knee joint prostheses.

SUMMARY

This section provides a general summary of the disclosure, and is not a comprehensive disclosure of its full scope or all of its features.

A femoral prosthesis for replacing a knee joint between a femur and a tibia can include a femoral component, a tibial component, a bearing and a yoke assembly. The femoral component can include a first condylar portion, a second condylar portion and an intercondylar portion having a first sidewall and a second sidewall. The tibial component can have a bone engaging inferior surface and a bearing engaging superior surface. The bearing can have an inferior surface that fixedly engages the bearing engaging superior surface of the tibial component and a superior femoral engaging surface. The yoke assembly can have a yoke disposed between the bearing and the femoral component and an axle having an axle axis and that hingedly couples the yoke with the femoral component. Rotation of the femoral component about a rotation axis that is perpendicular to the axle axis can cause concurrent rotation of the yoke about the rotation axis while the first and second condylar portions rotate along the superior femoral engaging surface of the bearing.

According to additional features, rotation of the yoke around the rotation axis can be limited to a fixed angle of rotation. The fixed angle of rotation can be substantially about twenty degrees. The bearing can define a pocket having at least one wall. The yoke can at least partially nest in the pocket. The yoke can engage the at least one wall thereby limiting further rotation.

According to other features, the prosthesis can further comprise a bearing support that is fixed to the bearing and that includes a shaft extending out of the bearing at the pocket. The shaft can be threadably coupled to a coupling nut within the yoke. The coupling nut can engage a surface of the yoke to preclude lift-off of the yoke away from the bearing. The bearing support can be formed of biocompatible metal and be molded into the bearing.

According to other features, a prosthesis for replacing a knee joint between a femur and a tibia can include a femoral component, a tibial component, a bearing and a yoke assembly. The bearing can have an inferior surface that fixedly engages the bearing engaging superior surface of the tibial component and a superior femoral engaging surface. The bearing can further have sidewalls that define a pocket on the superior femoral engaging surface. The yoke assembly can have a yoke disposed between the bearing and the femoral component and an axle having an axle axis. The axle can hingedly couple the yoke with the femoral component. Rotation of the femoral component about a rotation axis that is perpendicular to the axle axis causes concurrent rotation of the yoke about the rotation axis while the first and second condylar portions rotate along the superior femoral engaging surface of the fixed bearing. The yoke can be bound by and engage the sidewalls of the bearing at a maximum rotation.

According to other features, rotation of the yoke around the rotation axis is limited to a fixed angle of rotation. The fixed angle can be substantially about twenty degrees. The yoke can at least partially nest in the pocket.

The prosthesis can further comprise a bearing support that is fixed to the bearing and that includes a shaft that extends out of the bearing at the pocket. The shaft can be threadably coupled to a coupling nut within the yoke. The coupling nut can engage a surface of the yoke to preclude lift-off of the yoke away from the bearing. The bearing support can be formed of a biocompatible metal and be molded into the bearing.

According to other features, a prosthesis for replacing a knee joint between a femur and a tibia can include a femoral component, a tibial component, a bearing and a yoke assembly. The femoral component can include a first condylar portion, a second condylar portion and an intercondylar portion having a first sidewall and a second sidewall. The tibial component can have a bone engaging inferior surface and a bearing engaging superior surface. The bearing can have an inferior surface that fixedly engages the bearing engaging superior surface of the tibial component and a superior femoral engaging surface. The yoke assembly can have a yoke, a fastener, an axle having an axle axis, and a yoke base. The yoke can comprise at least two arms extending therefrom. The yoke base can have a body portion that defines a receiving portion. The fastener can be configured to be advanced into the yoke causing the at least two arms to radially expand and fixedly engage the yoke base at the receiving portion. The yoke and the yoke base can be configured to collectively rotate about a rotation axis that is perpendicular to the axle axis relative to the tibial component.

According to other features, the bearing can define insets thereon that rotationally bound corresponding tabs extending from the yoke base. Maximum rotation of the yoke and yoke base is attained when the tabs engage corresponding surfaces on the bearing at the insets. The prosthesis can further comprise a hyperextension stop disposed between the femoral component and the yoke.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a cross-sectional view taken along lines 3-3 of FIG. 1;

FIG. 4 is a cross-sectional view of the hinged knee joint prosthesis shown in FIG. 3 and illustrated with the femoral component shown in flexion;

FIG. 8 is a cross-sectional view taken along lines 8-8 of the hinged knee joint prosthesis of FIG. 6;

FIG. 9 is a cross-sectional view of the knee joint prosthesis shown in FIG. 8 and illustrated with the femoral component in flexion;

Corresponding reference numerals indicate corresponding parts throughout the several views of the drawings.

DETAILED DESCRIPTION

Example embodiments will now be described more fully with reference to the accompanying drawings.

The following description of the embodiments concerning a hinged knee joint prosthesis are merely exemplary in nature and are not intended to limit the disclosure or its application or uses. Moreover, while the present disclosure is described in detail below generally with respect to a hinged knee joint prosthesis, it will be appreciated by those skilled in the art that the present disclosure is clearly not limited to only a hinged knee joint prosthesis and may be applied to various other types of knee joint prostheses. Furthermore, it will be appreciated that the hinged knee joint prostheses disclosed herein may be used as part of a revision or primary knee joint procedure. Additionally, as used herein, some of the hinged knee joint prostheses are referred to as "convertible" and not "non-convertible". It will be appreciated that they are not so limited. In this regard, while some embodiments are referred to as "convertible", they need not necessary be required to convert various components thereof between implanted conditions including hinged and non-hinged.

Figure 1:
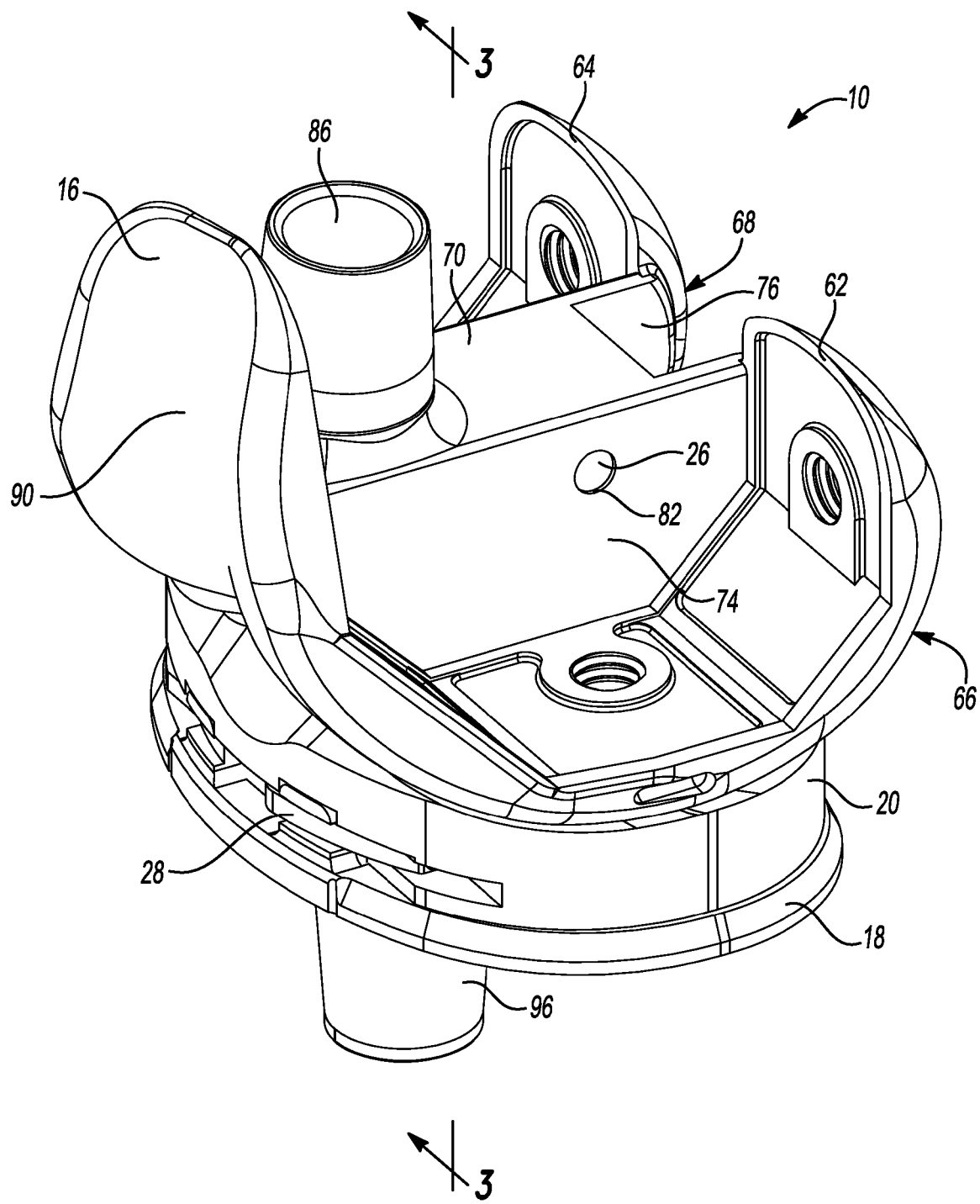
FIG. 1 is an anterior perspective view of a convertible hinged knee joint prosthesis having a constrained bearing and constructed in accordance with one example of the present teachings.
Figure 2:
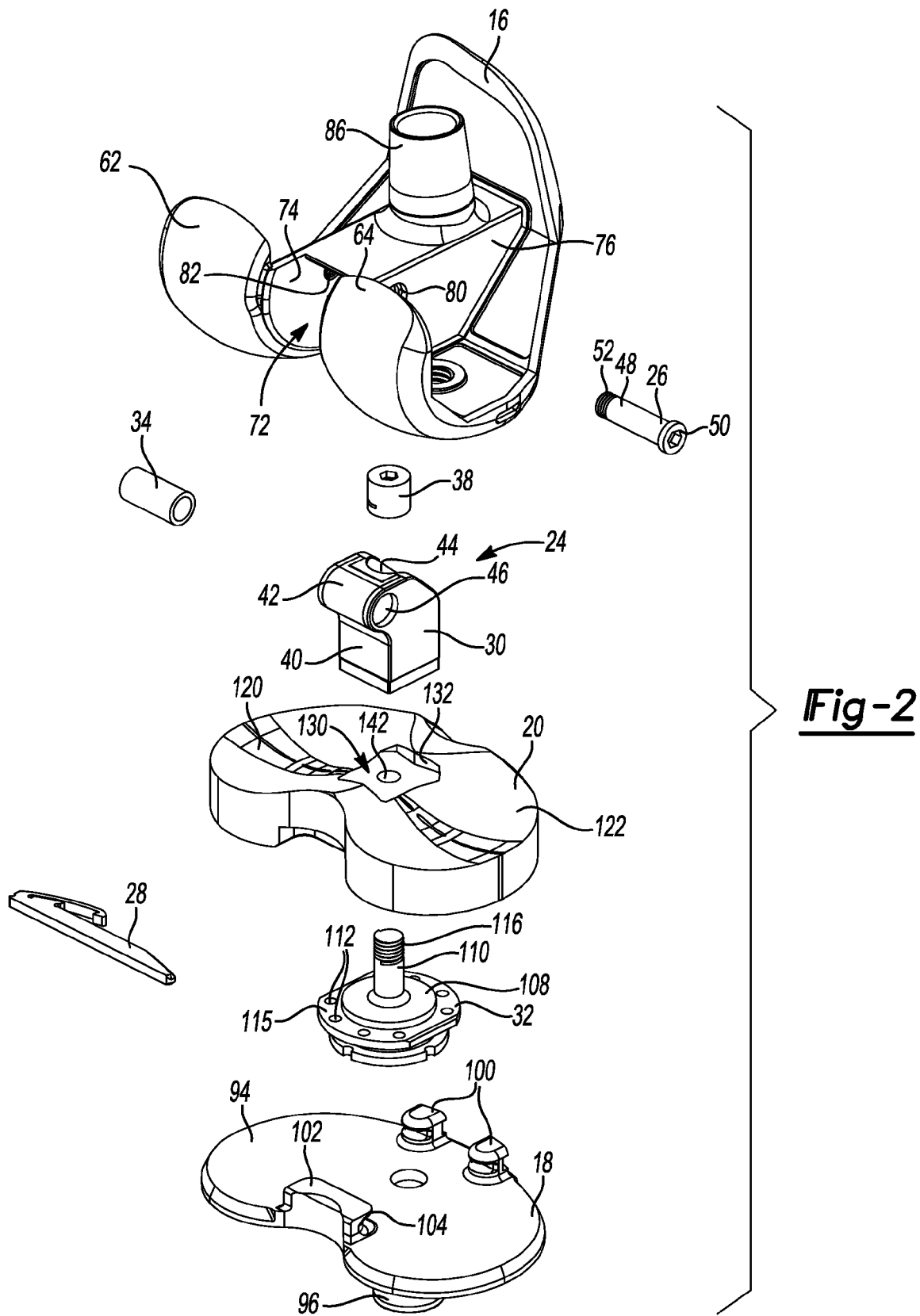
FIG. 2 is an exploded posterior perspective view of the knee joint prosthesis illustrated in FIG. 1.
Figure 5A:
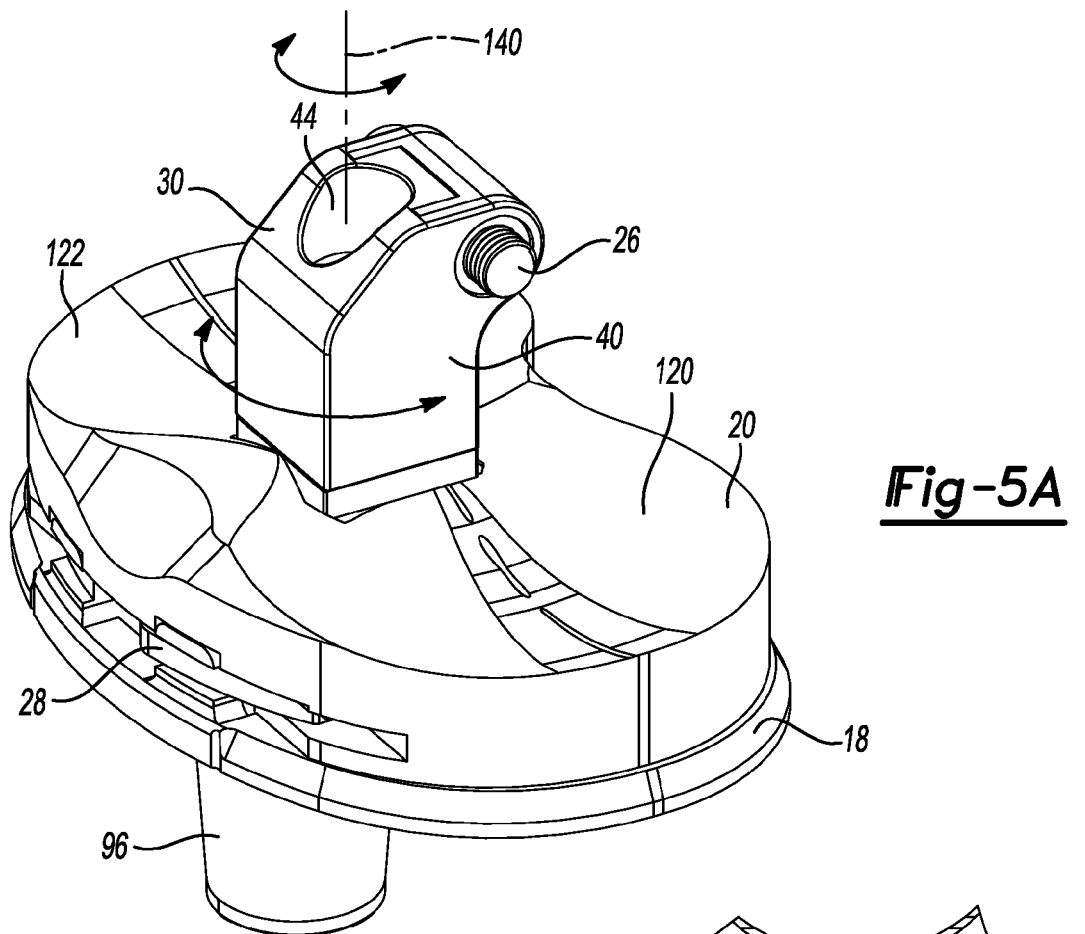
FIG. 5A is an anterior perspective view a yoke, a bearing and a tibial component of the hinged knee joint prosthesis of FIG. 1.
Figure 5B:
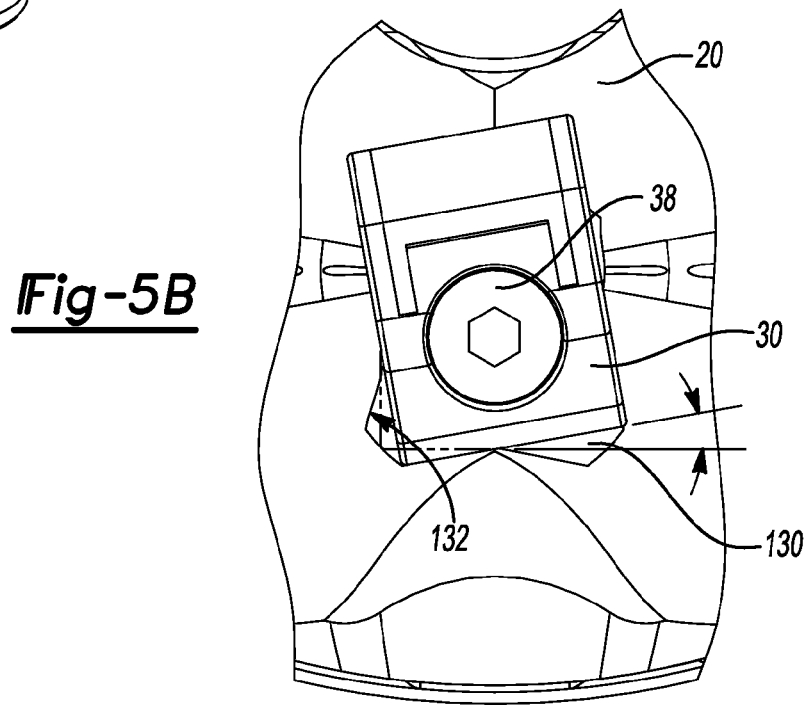
FIG. 5B is a plan view of the yoke rotating relative to the bearing.
Figure 6:
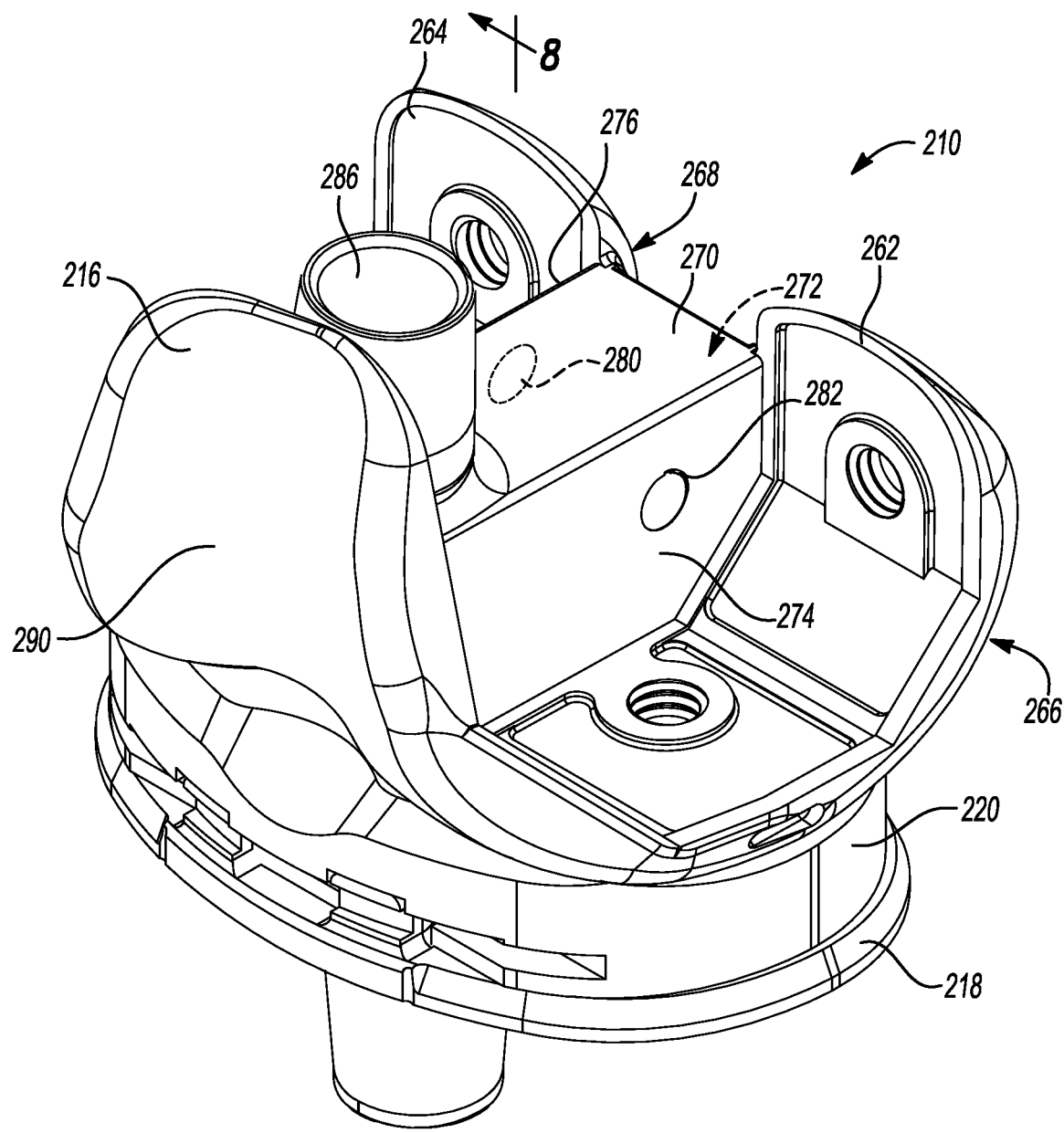
FIG. 6 is an anterior perspective view of a convertible hinged knee joint prosthesis having a floating bearing constructed in accordance with another example of the present teachings.

With initial reference to FIGS. 1 and 2, a knee joint prosthesis constructed in accordance to one example of the present teachings is shown and generally identified at reference numeral 10. The knee joint prosthesis 10 is generally shown as a hinged knee joint prosthesis 10, which is designed to provide adequate stability in case of moderate deterioration or instability of the human knee. This most typically occurs when the anterior and posterior cruciate ligaments are sacrificed or dysfunctional. In some examples, the medial and/or lateral collateral ligaments can be functionally intact or can also be dysfunctional. The hinged knee joint prosthesis 10 can be referred to as a convertible hinge prosthesis having a constrained bearing. The knee joint prosthesis 10 can generally include a femoral component 16, a tibial component 18, a bearing 20, a yoke assembly 24 (FIG. 2), an axle 26 and a locking bar 28. The yoke assembly 24 can include a yoke 30, a bearing support 32, an axle sleeve 34 and a coupling nut 38.

In one example, the yoke 30 can include a structural member 40 having a polymeric molded insert 42. The structural member 40 can be formed of a biocompatible metal such as, but not limited to, cobalt or titanium. The yoke 30 can have a recess 44 configured to receive the coupling nut 38. An axle passage 46 can be defined through the yoke 30. The axle sleeve 34 can be cannulated and formed of a polymer or a reinforced polyether ether ketone (PEEK). The axle 26 can include an axle shaft 48 that extends between a head 50 and a distal threaded end 52.

The femoral component 16 will be further described. The femoral component 16 can be adapted to be secured to a distal end of a femur and includes a first condylar portion 62 and a second condylar portion 64 that provide a first femoral bearing surface 66 and a second femoral bearing surface 68, respectively. The first and second condylar portions 62 and 64 of the femoral component 16 can be interconnected by an intercondylar portion 70 that has an intercondylar recess 72.

The intercondylar portion 70 can include a first lateral sidewall 74 and a second lateral sidewall 76 that are substantially planar and parallel to one another. In one example, the second lateral sidewall 76 can have an aperture 80 (FIG. 2) formed therethrough and the first lateral sidewall 74 can have a threaded aperture 82 formed therein. As will become appreciated from the following discussion, the threaded aperture 82 can be configured to mate with the distal threaded end 52 of the axle 26 in an assembled position. A superiorly extending portion 86 can be formed on the intercondylar portion 70. The superiorly extending portion 86 can be configured to selectively couple with various adapters and/or stems such as provided in the Vanguard Complete Knee System manufactured by Biomet Manufacturing Corp. of Warsaw, Ind. Further description of such components and their assembly to the femoral component 16 may be found in commonly owned and issued U.S. Pat. No. 8,187,280, issued on May 29, 2012, which is hereby incorporated by reference.

The femoral component 16 can further include an arcuate patellar portion 90, which is disposed on the anterior surface of the femoral component 16. The patellar portion 90 can be shaped to allow anatomical tracking of a natural or prosthetic patella. The patella prosthesis, which are compatible with the present disclosure may be a varying shape, such as round or dome-shaped and may be constructed from polyethylene, polyethylene with metal backing or other suitable materials. The femoral component 16 can be formed from biocompatible material, such as high strength alloys, including, but not limited to, cobalt-chromium, molybdenum alloy or other suitable material. All of the surfaces, which do not contact the femur, can be highly polished to provide smooth articulating bearing surfaces.

With reference now to FIGS. 2-5, the tibial component 18 will be further described. The tibial component 18 can be configured to be secured to a proximal end of a tibia after the tibia has been resected in a manner known in the art. The tibial component 18 can include a platform-like tibial tray 94 having an inferiorly extending tibial stem 96. The tibial stem 96 can be adapted to be received in a corresponding opening made by the surgeon in a longitudinal center of a tibia. The tibial tray 94 can have a pair of anterior posts 100 and a posterior tab 102. The posts 100 and the tab 102 are configured to cooperatively mate with the bearing 20 to secure the bearing 20 in a fixed relationship to the tibial component 18. In one example, the tab 102 can have a lip 104 (FIG. 3) configured to engage a corresponding ledge 106 provided on the bearing 20. In addition, the locking bar 28 can be slidably advanced between the locking posts 100 on the tibial component 18 and a corresponding lip 114 extending on the bearing 20. Additional description of the locking bar 28 and its engagement between the tibial component 18 and the bearing 20 may be found in commonly owned and currently pending U.S. patent application Ser. No. 13/483,111 filed on May 30, 2012.

With particular reference now to FIG. 2, the bearing support 32 will be described in greater detail. The bearing support 32 can have a generally disk shaped body portion 108 and stem portion 110. A series of apertures 112 can be formed through an annular flange 115. The stem portion 110 can include a distal threaded end 116.

With continued reference to FIGS. 2-5B, the bearing 20 will be described in greater detail. The bearing 20 can generally include a first bearing portion 120 and a second bearing portion 122. The first and second bearing portions 120 and 122 are configured to substantially mate with and provide an articulating surface to the first and second femoral bearing surfaces 62 and 64 (FIG. 1) of the femoral component 16. Formed between the first and second bearing portions 120 and 122 is an opening 126 (FIG. 3). The opening 126 can generally be configured to receive the bearing support 32 therein. In one example, the bearing support 32 can be molded into the bearing 20. The bearing 20 can be formed from a surgical grade, low friction, low wearing plastic, such as ultra-high molecular weight polyethylene (UHMWPE) or other suitable material.

The bearing 20 can also define a pocket 130 configured to nestingly receive a portion of the structural member 40. The pocket 130 can have a perimeter wall 132 that can bound a distal end of the structural member 40. In one example, the wall 132 can be configured to bound the yoke 30 of the structural member 40. During use, the structural member 40 is permitted to rotate around an axis 140 a pre-determined amount. In the example provided, the structural member 40 is permitted to rotate ten degrees in either direction. Again, it will be appreciated that rotation of the structural member 40 occurs while the bearing 20 is fixed relative to the tibial component 18. As a result, the femoral component 16 is permitted to rotate with the yoke 30 about twenty degrees around the axis 140 while the bearing 20 remains fixed relative to the tibial component 18.

In an assembled position (FIGS. 3 and 4), the stem portion 110 can extend out of the bearing 20 through an aperture 142 (FIG. 2) at a generally centralized location in the pocket 130. The distal threaded end 116 can be configured to threadably mate with the coupling nut 38 received in the recess 44 of the yoke 30. During assembly, the structural member 40 of the yoke 30 can be coupled to the femoral component 16 by passing the axle 26 through the aperture 80 in the femoral component, through the axle sleeve 34, and into the threaded aperture 82. After the axle 26 is threadably engaged to the aperture 82, the femoral component 16 is permitted to rotate about the axle 26 as shown in FIGS. 3 and 4.

With reference now to FIGS. 6-9, a knee joint prosthesis constructed in accordance to another example of the present teachings is shown and generally identified at reference numeral 210. The knee joint prosthesis 210 is generally shown as a hinged knee joint prosthesis 210, which is designed to provide adequate stability in case of moderate deterioration or instability of the human knee. Similar to the hinged knee prosthesis 10 described above, the hinged knee prosthesis 210 can be referred to as a convertible hinge prosthesis having a constrained bearing. The knee joint prosthesis 210 can generally include a femoral component 216, a tibial component 218, a bearing 220, a yoke assembly 224 (FIG. 7), an axle 226 and a locking bar 228. The yoke assembly 224 can include a yoke 230, a yoke base 232, an axle sleeve 234, a fastener 238 and a box 239.

The yoke 230 can be formed of a biocompatible metal such as, but not limited to, cobalt or titanium. The yoke 230 can have a distal end 240 including a plurality of radially disconnected arms 242. The yoke 230 can have a recess 244 configured to receive the fastener 238. A pair of tangs 245 can extend from the yoke 230. An axle passage 246 can be defined through the yoke 230. The axle sleeve 234 can be cannulated and formed of a polymer or a reinforced PEEK. The axle 226 can include an axle shaft 248 that extends between a head 250 and a distal threaded end 252.

The femoral component 216 will be further described. The femoral component 216 can be adapted to be secured to a distal end of a femur and includes a first condylar portion 262 and a second condylar portion 264 that provide a first femoral bearing surface 266 and a second femoral bearing surface 268, respectively. The first and second condylar portions 262 and 264 of the femoral component 216 can be interconnected by an intercondylar portion 270 that has an intercondylar recess 272.

The intercondylar portion 270 can include a first lateral sidewall 274 and a second lateral sidewall 276 that are substantially planar and parallel to one another. In one example, the second lateral sidewall 276 can have an aperture 280 (FIG. 6) formed therethrough and the first lateral sidewall 274 can have a threaded aperture 282 formed therein. As will become appreciated from the following discussion, the threaded aperture 282 can be configured to mate with the distal threaded end 252 of the axle 226 in an assembled position. A superiorly extending portion 286 can be formed on the intercondylar portion 270. The superiorly extending portion 286 can be configured to selectively couple with various adapters and/or stems as discussed above. The femoral component 216 can further include an arcuate patellar portion 290, which is disposed on the anterior surface of the femoral component 216. The patellar portion 290 can be shaped to allow anatomical tracking of a natural or prosthetic patella. The patella prosthesis, which are capable with the present disclosure, may be a varying shape, such as round or dome shaped, and may be constructed as described above. The femoral component 216 can be formed from a biocompatible material, such as high strength alloys as described above.

Figure 7:
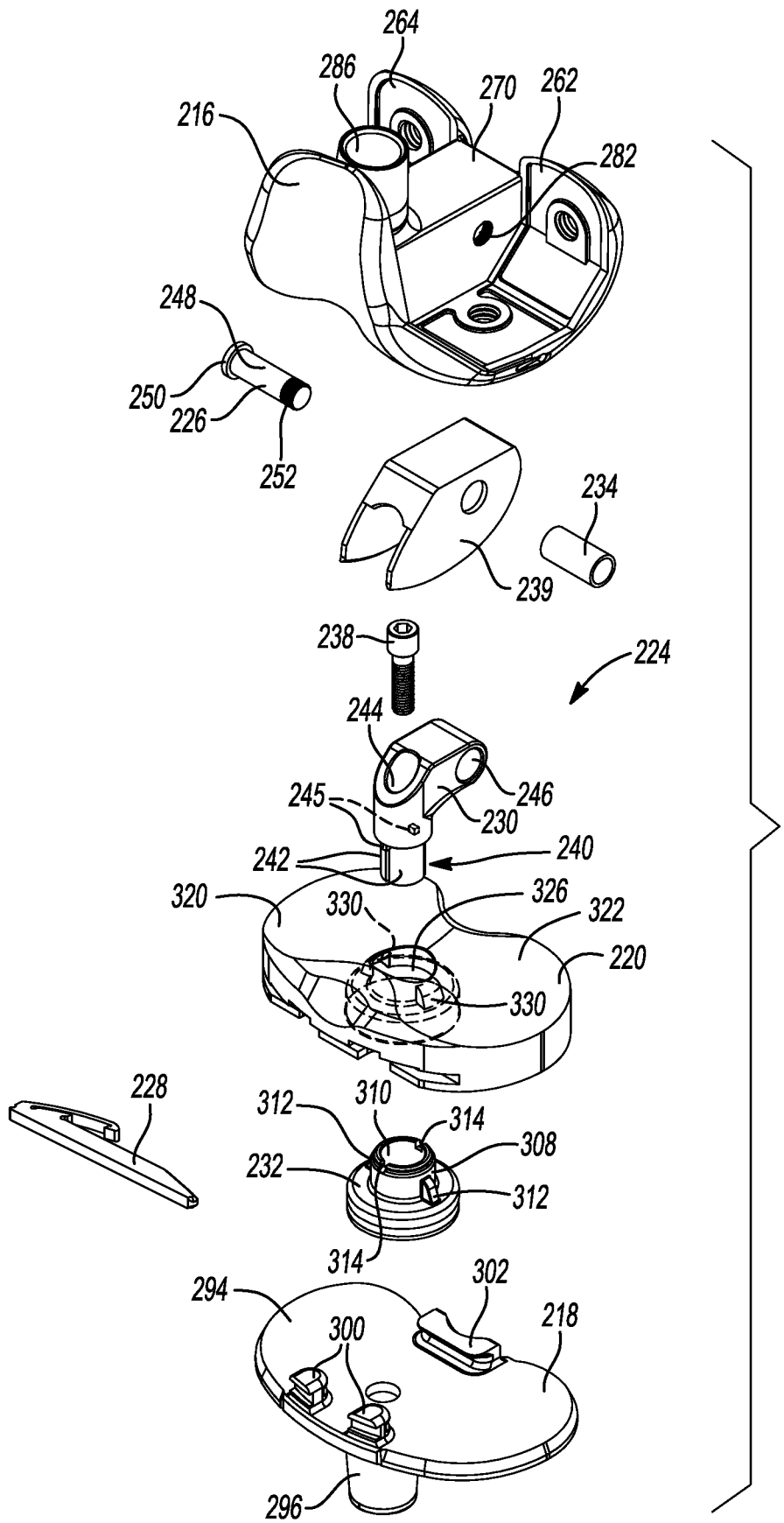
FIG. 7 is an anterior perspective exploded view of the hinged knee joint prosthesis of FIG. 6.
Figure 10:
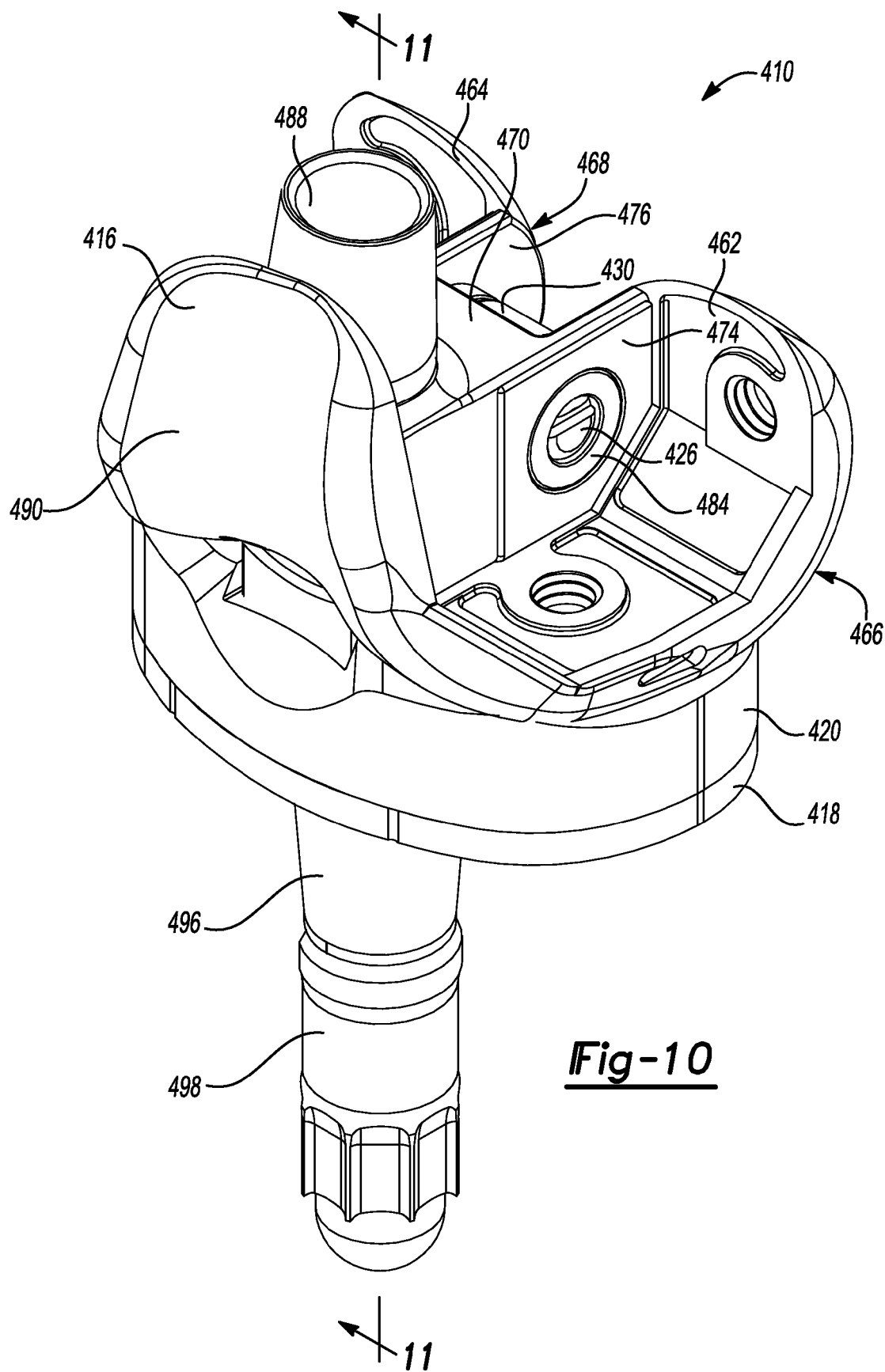
FIG. 10 is a posterior perspective view of a non-convertible hinged knee joint prosthesis constructed in accordance to another example of the present teachings.

With particular reference now to FIGS. 7-9, the tibial component 218 will be further described. The tibial component 218 can be secured to a proximal end of a tibia after the tibia has been resected. The tibial component 218 can include a platform-like tray 294 having an inferiorly extending stem 296. The tibial stem 296 can be adapted to be received in a corresponding opening made by a surgeon in a longitudinal center of the tibia. The tibial tray 294 can have a pair of anterior posts 300 and a posterior tab 302. The posts 300 and the tab 302 are configured to cooperatively mate with the bearing 220 to secure the bearing 220 in a fixed relationship to the tibial component 218. The tab 302 can have a lip 304 (FIG. 8) configured to engage a corresponding ledge 306 provided on the bearing 220. In addition, the locking bar 228 can be slidably advanced between the locking posts 300 on the tibial component 218 and a corresponding lip 305 extending on the bearing 220.

With continued reference now to FIGS. 7-9, the yoke base 232 will be described in greater detail. The yoke base 232 can have a generally disk-shaped body portion 308 and a receiving portion 310. A pair of tabs 312 can extend from the body portion 308. A pair of notches 314 can be defined on the body portion 308.

The bearing 220 will now be described in greater detail. The bearing 220 can generally include a first bearing portion 320 and a second bearing portion 322. The first and second bearing portions 320 and 322 are configured to substantially mate with and provide an articulating surface to the first and second femoral bearing surfaces 262 and 264 of the femoral component 216. Formed between the first and second bearing portions 320 and 322 is an opening 326. The opening 326 can generally be configured to receive the receiving portion 310 of the yoke base 232 and the distal tip 247 of the yoke 230. A pair of insets 330 can be formed in the bearing 220 configured to receive the tabs 312 on the yoke base 232. The tabs 312 are bound for rotation by the insets 330. In one example, the yoke base 232 rotates relative to the bearing 220 while the bearing 220 is fixed to the tibial component 218. The yoke base 232 can be configured to rotate about 20 degrees relative to the bearing 220. In this regard, the yoke base 232, yoke 230 and femoral component 216 can rotate relative to the bearing 220. The bearing 220 may be formed of similar materials as discussed above with respect to the bearing 20.

In an assembled position (FIGS. 8 and 9), the fastener 238 can extend into the recess 244 of the yoke 230 and further into the receiving portion 310 of the yoke base 232. Insertion of the fastener 238 can cause the arms 242 to extend radially outwardly and engage the receiving portion 310 in a fixed position. The tangs 245 of the yoke 230 can be nestingly received by the notches 314 on the yoke base 232.

During assembly, the yoke 230 and box 239 can be coupled to the femoral component 216 by passing the axle 226 through the aperture 280 in the femoral component, through the first aperture in the box 239, through the sleeve 234 and out the second aperture in the box 239. The threaded end 252 can then threadably mate with the threaded aperture 282. After the axle 226 is threadably engaged to the aperture 282, the femoral component 216 is permitted to rotate about the axle 226 as shown in FIGS. 8 and 9.

Turning now to FIGS. 10-13, a knee joint prosthesis constructed in accordance to another example of the present teachings is shown and generally identified at reference numeral 410. The knee joint prosthesis 410 is generally shown as a hinged knee joint prosthesis 410, which is designed to provide adequate stability in case of moderate deterioration or instability of the human knee. The hinged knee joint prosthesis 410 can be referred to as a non-convertible hinge prosthesis. The knee joint prosthesis 410 can generally include a femoral component 416, a tibial component 418, a bearing 420, a yoke assembly 424 (FIG. 12), an axle 426 and a hyperextension bumper 428. The yoke assembly 424 can include a yoke 430, a hinge post 432 and a tibial bushing 434.

The yoke 430 can generally include a yoke base 440 and a yoke keel 442. The yoke base 440 can define a passage 444. The yoke keel 442 can define an axle passage 446 and a pin passage 448. The yoke 430 can be formed of a biocompatible metal such as, but not limited to, cobalt or titanium. The passage 444 of the yoke base 440 can be configured to receive the tibial bushing 434. The tibial bushing 434 can be formed of PEEK.

Figure 12:
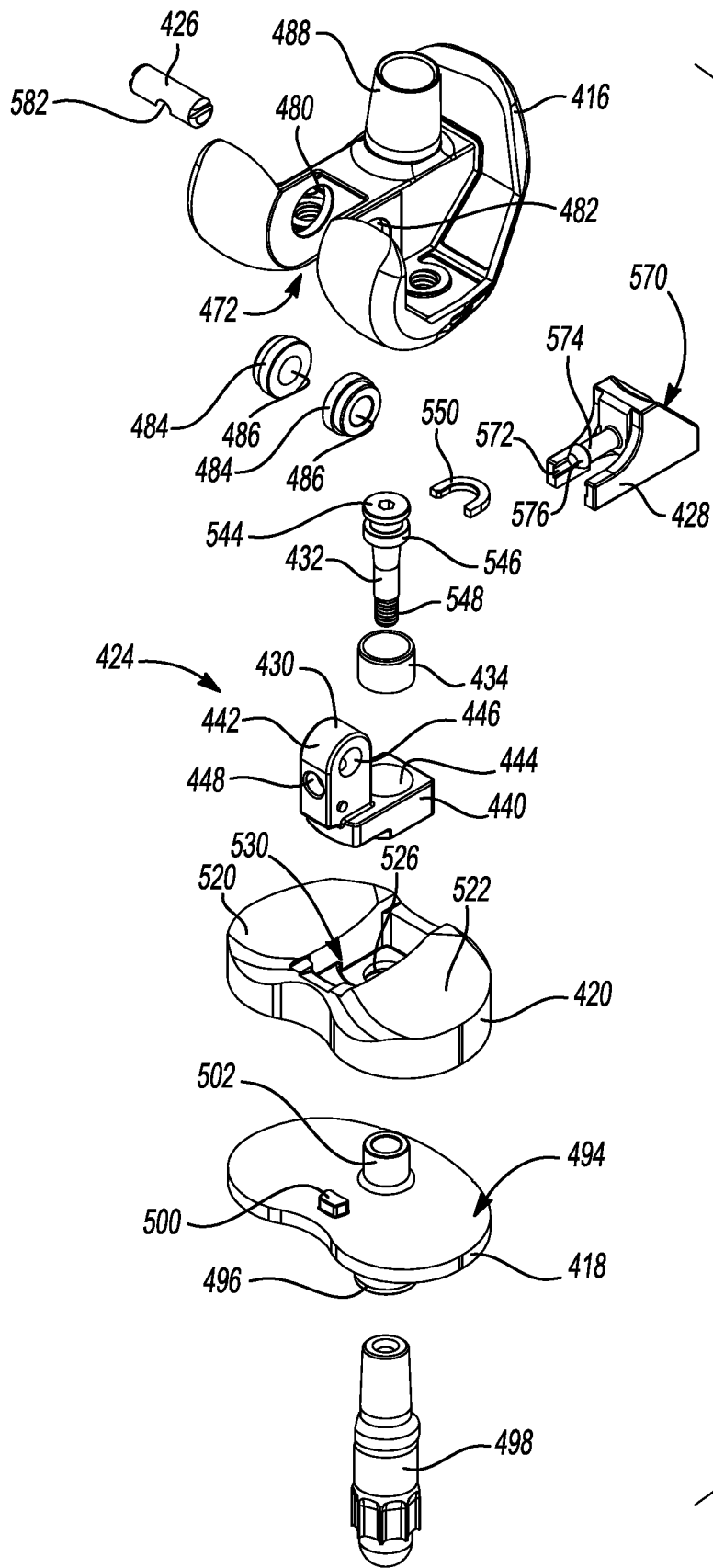
FIG. 12 is a posterior perspective exploded view of the hinged knee joint prosthesis of FIG. 10.

The femoral component 416 will now be further described. The femoral component 416 can be adapted to be secured to a distal end of a femur and includes a first condylar portion 462 and a second condylar portion 464 that provide a first femoral bearing surface 466 and a second femoral bearing surface 468, respectively. The first and second condylar portions 462 and 464 of the femoral component 416 can be interconnected by an intercondylar portion 470 that has an intercondylar recess 472 (FIG. 12). The intercondylar portion 470 can include a first lateral sidewall 474 and a second lateral sidewall 476 that are substantially planar and parallel to one another. In one example, the first and second lateral sidewalls 474 and 476 can define openings 480 and 482, respectively for receiving bushings 484 therein. The bushings 484 can be formed of polyethylene. The bushings 484 define passages 486 that are configured to receive the axle 426 in an assembled position as will become appreciated from the following discussion.

A superiorly extending portion 488 can be formed on the intercondylar portion 470. The superiorly extending portion 488 can be configured to selectively couple with various adapters and/or stems such as identified above.

The femoral component 416 can further include an arcuate patellar portion 490, which is disposed on the anterior surface of the femoral component 416. The patellar portion 490 can be shaped to allow anatomical tracking of a natural or prosthetic patella. The patella prosthesis, which are compatible with the present disclosure may be a varying shape, such as round or dome-shaped and may be constructed from polyethylene, polyethylene with metal backing or other suitable materials. The femoral component 416 can be formed from biocompatible metal such as those identified above. All of the surfaces, which do not contact the femur, can be highly polished to provide smooth articulating bearing surfaces.

Figure 11:
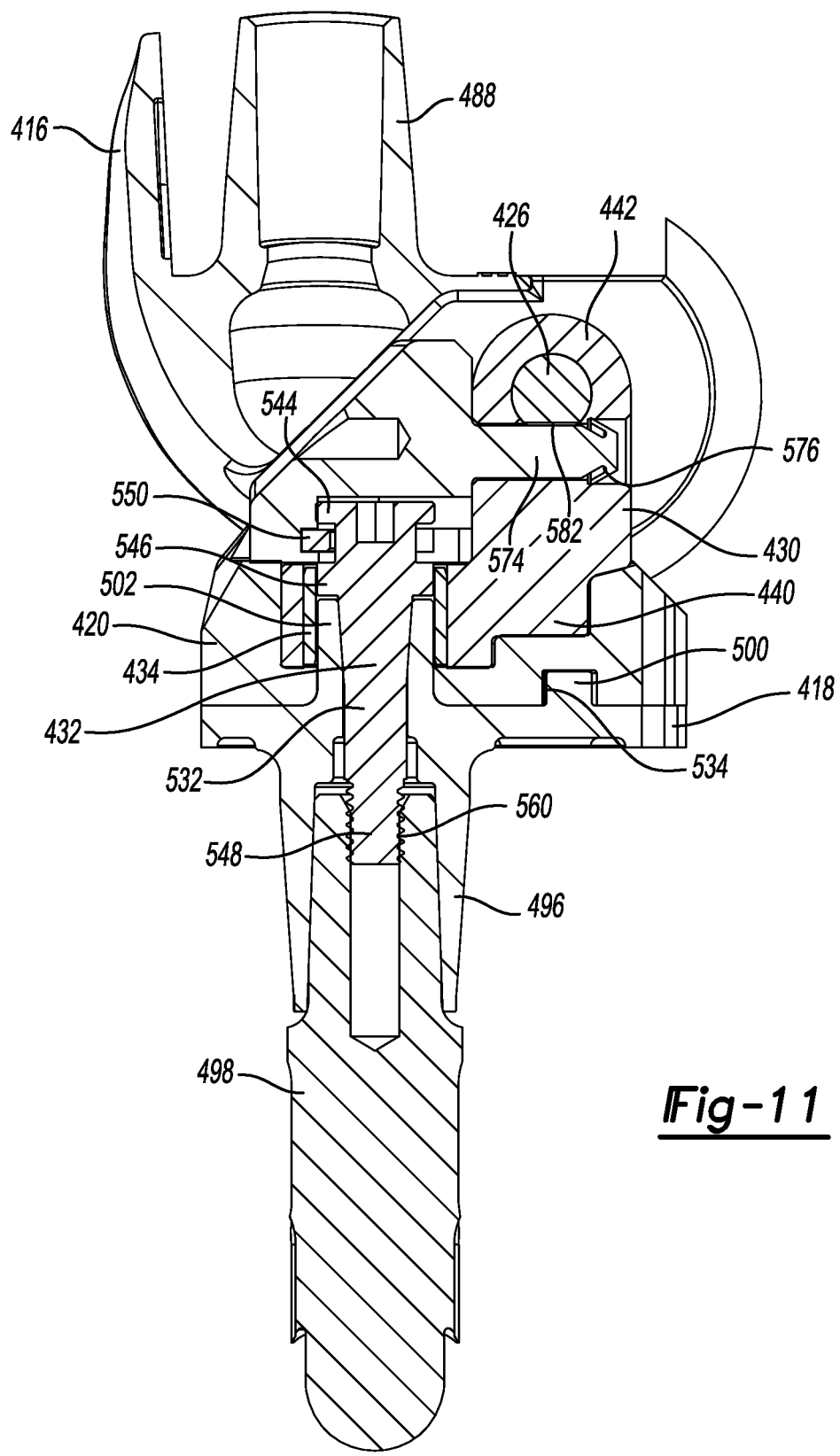
FIG. 11 is a cross-sectional view taken along lines 11-11 of the hinged knee joint prosthesis of FIG. 10.
Figure 13:
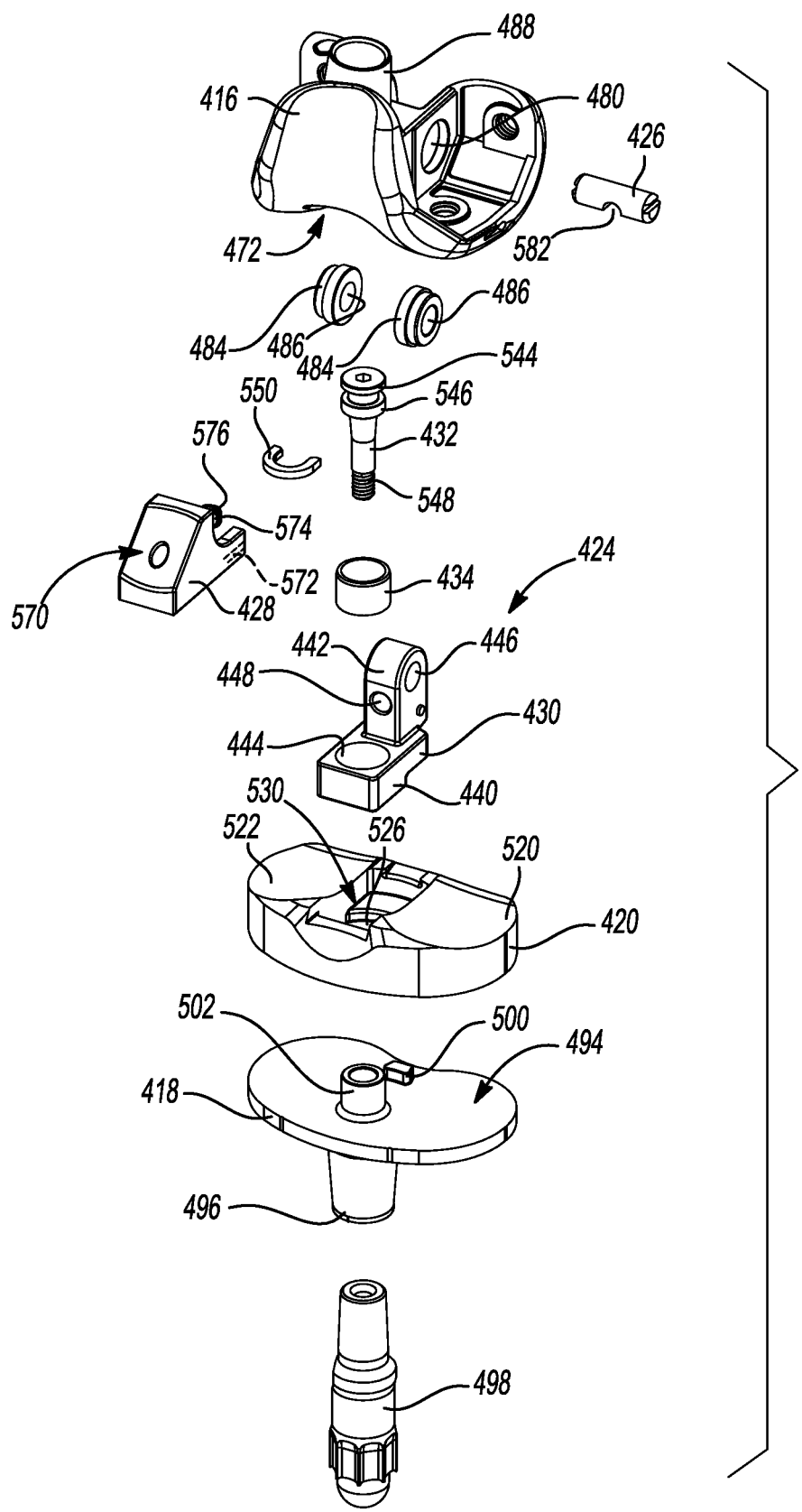
FIG. 13 is an anterior perspective exploded view of the hinged knee joint prosthesis shown in FIG. 10.

With reference now to FIGS. 11-13, the tibial component 418 will be further described. The tibial component 418 can be configured to be secured to a proximal end of a tibia after the tibia has been resected in a manner known in the art. The tibial component 418 can include a platform-like tibial tray 494 having an inferiorly extending tibial stem 496. The inferiorly extending tibial stem 496 can be configured to mate with a corresponding stem extension 498. The tibial tray 494 can include a polished surface to reduce the coefficient of friction during slidable rotation of the bearing 420 as will become appreciated. The tray 494 can further include a stop 500 extending therefrom. The tibial component 418 can further include a superiorly extending boss 502.

With continued reference now to FIGS. 11-13, the bearing 420 can generally include a first bearing portion 520 and a second bearing portion 522. The first and second bearing portions 520 and 522 are configured to substantially mate with and provide an articulating surface to the first and second femoral bearing surfaces 462 and 464 (FIG. 1) of the femoral component 416. Formed between the first and second bearing portions 520 and 522 is an opening 526 (FIG. 12). The opening 526 can be generally configured to receive the boss 502 of the tibial component 418 and the hinge post 432 (FIG. 11). The bearing 420 can also define a pocket 530 configured to nestingly receive a portion of the yoke 430. The bearing 420 can also define a stop groove 534 that cooperatively receives the stop 500 of the tibial component 418 (FIG. 11). As will become appreciated, the stop groove 534 can be configured to slidably guided relative to the stop 500 to allow up to a predetermined amount of movement in internal and external rotation of the bearing 420 relative to the tibial component 418. In the particular example, the bearing 420 is permitted to rotate up to twenty degrees of movement in internal and external rotation. The bearing 420 can be formed from a surgical grade, low friction, low wearing plastic, such as UHMPE or other suitable material.

The hinge post 432 will now be described in greater detail. The hinge post 432 can generally include a head 544, a collar 546 and a distal threaded tip 548. A metal clip 550 is configured to nest between the head 544 and the collar 546 in an assembled position (FIG. 11). The hinge post 432 is configured to pass through the tibial bushing 434, the passage 444, the bearing pocket 530, the boss 502 and the opening 526. The threaded distal tip 548 can be configured to threadably mate with a corresponding threaded receiving portion 560 provided on the stem extension 498 (FIG. 11).

The hyperextension bumper 428 can generally include a hyperextension surface 570, a clip track 572 and a pin 574. The pin 574 can have a head 576 configured on a distal tip. The track 572 can be configured to nestingly receive the clip 550. In an assembled position, the pin 574 is configured to be received into the pin passage 448 of the yoke 430. In one example, the head 576 can engage a counterbore formed on the yoke keel 442 at the pin passage 448 (see FIG. 11). The pin 574 can slidably engage a groove 582 defined in the axle 426 to inhibit movement of the axle 426 along its axis in an assembled position.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A prosthesis for replacing a knee joint between a femur and a tibia, the prosthesis comprising:

a femoral component including a first condylar portion, a second condylar portion and an intercondylar portion having a first sidewall and a second sidewall;

a tibial component having a bone engaging inferior surface and a bearing engaging superior surface;

a bearing having an inferior surface that engages the bearing engaging superior surface of the tibial component and a superior femoral engaging surface, the bearing defines a pocket; and a yoke assembly having a yoke base seated in the pocket and a yoke disposed between the bearing and the femoral component, cooperation between the yoke base and the pocket restricts rotation of the yoke assembly relative to the bearing; and an axle having an axle axis and that hingedly couples the yoke with the femoral component;

wherein rotation of the femoral component about a rotation axis that is perpendicular to the axle axis causes concurrent rotation of the yoke about the rotation axis while the first and second condylar portions rotate along the superior femoral engaging surface of the bearing.

2. The prosthesis system of claim 1 wherein rotation of the bearing is limited to a fixed angle of rotation.

3. The prosthesis system of claim 2 wherein the fixed angle is substantially twenty degrees.

4. The prosthesis system of claim 2 wherein the bearing defines at least one wall at the pocket.

5. The prosthesis of claim 1, wherein the yoke base defines a passage configured to receive a fastener therethrough for coupling the yoke and the bearing to the tibial component, a pin passage, and an axle passage configured to receive the axle therethrough.

6. The prosthesis of claim 5, further comprising a hyperextension stop including a pin configured for receipt in the pin passage to retain the hyperextension stop between the femoral component and the yoke base.

7. A prosthesis for replacing a knee joint between a femur and a tibia, the prosthesis comprising:

a femoral component including a first condylar portion, a second condylar portion and an intercondylar portion having a first sidewall and a second sidewall;

a tibial component having a bone engaging inferior surface and a bearing engaging superior surface;

a bearing having an inferior surface that engages the bearing engaging superior surface of the tibial component and a superior femoral engaging surface, the bearing further having sidewalls that define a pocket on the superior femoral engaging surface; and a yoke assembly having a yoke disposed between the bearing and the femoral component and an axle having an axle axis and that hingedly couples the yoke with the femoral component, a portion of the yoke assembly is seated within the pocket such that the yoke is bound by the sidewalls defining the pocket and rotation of the yoke assembly is restricted by the sidewalls;

wherein rotation of the femoral component about a rotation axis that is perpendicular to the axle axis causes concurrent rotation of the yoke and the bearing about the rotation axis while the first and second condylar portions rotate along the superior femoral engaging surface of the bearing.

8. The prosthesis of claim 7 wherein rotation of the yoke around the rotation axis is limited to a fixed angle of rotation.

9. The prosthesis of claim 8 wherein the fixed angle is substantially twenty degrees.

10. The prosthesis of claim 7, wherein the yoke assembly further comprises a yoke base defining a passage configured to receive a fastener therethrough for coupling the yoke and the bearing to the tibial component, a pin passage, and an axle passage configured to receive the axle therethrough.

11. The prosthesis of claim 10, further comprising a hyperextension stop including a pin configured for receipt in the pin passage to retain the hyperextension stop between the femoral component and the yoke base.

12. The prosthesis of claim 11, wherein the pin is configured for receipt in a groove of the axle to retain the axle in the axle passage.

13. A prosthesis for replacing a knee joint between a femur and a tibia, the prosthesis comprising:

a femoral component including a first condylar portion, a second condylar portion and an intercondylar portion having a first sidewall and a second sidewall;

a tibial component having a bone engaging inferior surface and a bearing engaging superior surface;

a bearing having an inferior surface that fixedly engages the bearing engaging superior surface of the tibial component and a superior femoral engaging surface, the bearing including sidewalls defining a pocket;

a yoke assembly including, a yoke base nestingly seated within the pocket such that rotation of the yoke assembly is restricted by the sidewalls, a yoke, a fastener, and an axle having an axle axis, the yoke comprising a yoke base defining a passage configured to receive the fastener therethrough, an axle passage configured to receive the axle for rotation about the axle axis, and a pin passage extending generally perpendicular to the axle passage; and a hyperextension stop disposed between the femoral component and the yoke, the hyperextension stop includes a pin configured to extend into the pin passage and couple the hyperextension stop to the yoke;

wherein the yoke and yoke base are configured to collectively rotate about a rotation axis that is perpendicular to the axle axis relative to the tibial component, and cooperation between the yoke base and the sidewalls of the pocket prevents independent rotation of the yoke assembly relative to the bearing.

* * * * *

UNITED STATES PATENT AND TRADEMARK OFFICE
CERTIFICATE OF CORRECTION

| | | |
|---|---|---|
| PATENT NO. | : 8,936,648 B2 | Page 1 of 1 |
| APPLICATION NO. | : 13/796440 | |
| DATED | : January 20, 2015 | |
| INVENTOR(S) | : Curt Collard et al. | |

It is certified that error appears in the above-identified patent and that said Letters Patent is hereby corrected as shown below:

On the title page, item (71) Applicant: Delete "Biomet Manufacturing Corporation" and insert --Biomet Manufacturing, LLC--.

Signed and Sealed this
Nineteenth Day of May, 2015

Michelle K. Lee
*Director of the United States Patent and Trademark Office*